(12) United States Patent
Ramos et al.

(10) Patent No.: US 7,348,421 B1
(45) Date of Patent: Mar. 25, 2008

(54) METHODS FOR PRODUCTION OF P-HYDROXYBENZOATE IN BACTERIA

(75) Inventors: Juan-Luis Ramos, Granada (ES); Patricia Godoy-Alba, Granada (ES); Arie Ben-Bassat, Newark, DE (US); Maria-Isabel Ramos-Gonzalez, Granada (ES); Estrella Duque, Granada (ES)

(73) Assignee: North Carolina State University, Raleigh, NC (US)

( * ) Notice: Subject to any disclaimer, the term of this patent is extended or adjusted under 35 U.S.C. 154(b) by 287 days.

(21) Appl. No.: 10/754,648

(22) Filed: Jan. 12, 2004

Related U.S. Application Data

(63) Continuation of application No. 09/968,122, filed on Oct. 1, 2001, now abandoned.

(60) Provisional application No. 60/236,879, filed on Sep. 29, 2000.

(51) Int. Cl.
C07H 21/04 (2006.01)
C12N 1/21 (2006.01)
C12N 9/00 (2006.01)

(52) U.S. Cl. .................. 536/23.2; 536/23.7; 435/183; 435/252.3; 435/252.33; 435/252.34

(58) Field of Classification Search ............... 536/23.2; 435/183
See application file for complete search history.

(56) References Cited

U.S. PATENT DOCUMENTS

| 4,657,863 A | 4/1987 | Maxwell et al. |
| 4,810,648 A | 3/1989 | Stalker |
| 4,968,612 A | 11/1990 | Hsieh |
| 5,602,014 A | 2/1997 | Mizumura et al. |
| 5,635,391 A | 6/1997 | Petre et al. |
| 5,858,736 A | 1/1999 | Di Cosimo et al. |
| 6,030,819 A | 2/2000 | Amaratunga et al. |

FOREIGN PATENT DOCUMENTS

| CA | 2103616 | 2/1994 |
| JP | 5328981 | 12/1993 |
| JP | 5336979 | 12/1993 |
| JP | 5336980 | 12/1993 |
| WO | WO 9856920 | 12/1998 |
| WO | WO 99/23224 | 5/1999 |

OTHER PUBLICATIONS

Dan Cowen, et al., Biochemistry and biotechnology of mesophilic and thermophilic nitrite metabolizing enzymes, Extremophiles (1998) pp. 207-216, vol. 2, London.

Michihiko Kobayashi, et al., Nitrilase in biosynthesis of the plant hormone indole-3-acetic acid from indole-3-acetonitrite: Cloning of the Alcaligenes gene and site-directed mutagenesis of cysteine residues, Proc. Natl. Acad. Sioe, USA (Jan. 1993), pp. 247-251, vol. 90, Japan.

Michihiko Kobayashi, et al., Monohydrolysis of an aliphatic dinitrile compound by nitrilase from *Rhodococcus rhodochrous* k22, Tetrahedron (1990) pp. 5587-5590, vol. 46, No. 16, Great Britain.

Toru Nagasawa, et al., The superiority of the third-generation catalyst, *Rhodoccus rhodochrous* J1 nitrile hydratase, for industrial production of acrylamide, Appl. Microbiol Biotechnol (1993) pp. 189-195, vol. 40, Japan.

Michihiko Kobayashi, et al., Nitrilase from *Rhodococcus rhodochrous* J1, The Journal of Biological Chemistry (1992) pp. 20746-20751, vol. 267, No. 29, Japan.

Michihiko Kobayashi, et al., Primary structure of an aliphatic nitrile-degrading enzyme, aliphatic nitrilase, from *Rhodococcus rhodochrous* K22 and expression of its gene and identification of its active site residue, Biochemistry (1992) pp. 9000-9007, vol. 31, Japan.

Rebecco Cramp, et al., Novel thermophilic bacteria producing nitrite-degrading enzymes, Microbiology (1997) pp. 2313-2320, vol. 143, London.

Sophie Levy-Schil, et al., Aliphatic nitrilase from a soil-isolated *Comamonas testosteroni* sp.:gene cloning and overexpression, purification and primary structure, Gene (1995) pp. 15-20, vol. 161, France.

Michihiko Kobayashi, et al., Purification and characterization of a novel nitrilase of *Rhodococcus rhodochrous* K22 that acts on aliphatic nitrites. Journal of Bacteriology (Sep. 1990) pp. 4807-4815, vol. 172, No. 9, Japan.

Bitter et al., "Identification and characterization of the *exbB*, *exbD* and *tonB* genes of *Pseudomonas putida* WCS358: their involvement in ferric-pseudobactin transport," *Molecular Microbiology* 7(1): 117-130 (1993).

Godoy et al., "Involvement of the TonB System in Tolerance to Solvents and Drugs in *Pseudomonas putida* DOT-TIE," *Journal of Bacterbiology* 183(18): 5285-5292 (2001).

International Search Report, PCT/US01/31180, mailed Jul. 26, 2002.

(Continued)

Primary Examiner—Elizabeth Slobodyansky
(74) Attorney, Agent, or Firm—Myers, Bigel, Sibley & Sajovec, P.A.

(57) ABSTRACT

This invention relates to the isolation of a novel tonB operon from *Pseudomonas putida*. These genes are useful to render the cells more sensitive to antibiotics, toluene, pHBA, aromatic compounds, parabenes, and aromatic amino acids after inactivation with specific mutant allels or more tolerant to these compounds after overexpression with appropriate expression vector. These findings are important in the field of medicine and biotechnology and biocatalysis. In addition a screen to identify pHBA tolerant genes is provided and strains with significant tolerance to pHBA were identified. These strains are important for pHBA production.

5 Claims, 2 Drawing Sheets

OTHER PUBLICATIONS

Figure 1:
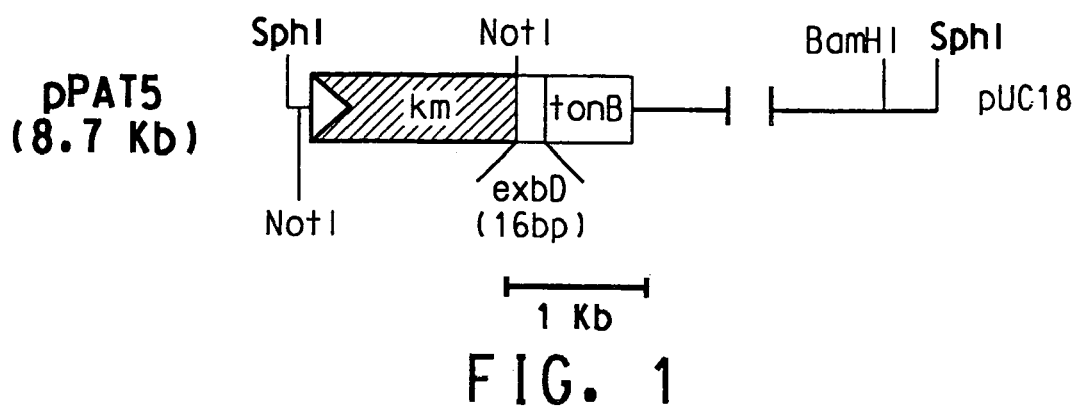

Kline et al., "Antimicrobial Effects of Novel Siderophores Linked to β-Lactam Antibiotics," *Bioorganic & Medicinal Chemistry* 8: 73-93 (2000).

Mosqueda et al., "A Set of Genes Encoding a Second Toluene Efflux System in *Pseudomonas putida* DOT-T1E is Linked to the *tod* Genes for Toluene Metabolism," *Journal of Bacteriology* 182(4): 937-943 (2000).

Ramos et al., "Isolation and Expansion of the Catabolic Potential of a *Pseudomonas putida* Strain Able To Grow in the Presence of High Concentrations of Aromatic Hydrocarbons," *Journal of Bacteriology* 177(14): 3911-3916 (1995).

Ramos-González et al., "Physiological Characterization of *Pseudomonas putida* DOT-T1E Tolerance to *p*-Hydroxybenzoate," *Applied and Environmental Microbiology* 67(9): 4338-4341 (2001).

Segura et al., "Multiple responses of Gram-negative bacteria to organic solvents," *EnvironmentalMicrobiology* 1(3): 191-198 (1999).

Zhao et al., "Influence of the TonB Energy-Coupling Protein on Efflux-Mediated Multidrug Resistance in *Pseudomonas aeruginosa*," *Antimicrobial Agents and Chemotherapy* 42(9): 2225-2231 (1998).

SEQUENCE LISTING

<160> NUMBER OF SEQ ID NOS: 11

<210> SEQ ID NO 1
<211> LENGTH: 2625
<212> TYPE: DNA
<213> ORGANISM: Pseudomonas putida

<400> SEQUENCE: 1

```
atcgacatag gctgcttggt aacccgcctc atcgtgctgg ctggccgcca cgcagtacac    60
caggtagtcc agcgggccct gtggcctggc ctgcgtatc gacggttcgg ccaaatctgc   120
ggcaaccggc tgaaccctg cgggcagctg accaacagaa cggcgcaggc cgctcacctg   180
ccagccttta gccaacatct gcttggccag acgcccaccc acatcaccac aacccaccac   240
catcacggaa aggtctgaca tctctaaact ccctagacca attgatcagc ctggccacgc   300
tacacgatgg gcggctagac cataggcgaa aaaagctaca atattacttt tgttaacaag   360
aattacttgc aataatggcc gccaaattgt tctcggccta catcgaggcc ttggagaacg   420
ttcacttttt cttcatcagg tccggccagc atgacacgta ctcaaccttc cgcttcgcca   480
accccgtcgc gcgcctggcg cgccatcgcc gcgctgacac tcagcctggt gctggccccg   540
gtggccatgg ccgatgagcc aaccaccaac gccgccacac ctgcggctgc tactgccccg   600
gccgcacccg ctgctgcccc ggtcgatgcg ccggcgcctg gtgccactgc caccaacccg   660
gcagatgcag acccaagcgt tcaagccctg gtcgaagaca cctcgctggg catggcccat   720
gacctgtccc catgggcat gtacaagaac gccgacatcg tggtgaagat cgtcatgatc   780
ggtctggcca tcgcctccat catcacctgg accatctgga ttgccaaagg cttcgagctg   840
atgggcgcca agcgtcgcct gcggggtgaa atcgcccagt tgaagaagtc caccaccctg   900
aaggaagcca gcgaagtctc caacaaggaa ggcaccctgg cccacaccct ggtccacgat   960
gccctcgaag agatgcgtct ttcggctaac gctcgcgaaa agaaggcat caaggagcgc  1020
gtcagcttcc gtctggagcg cctggtgcat gccagcggcc gcaccatgag cagcggcacc  1080
ggcgtcctcg caaccatcgg ctccaccgca ccgttcgttg gcctgttcgg taccgtatgg  1140
ggcatcatga acagcttcat cggcatcgcc aagacccaga ccaccaacct ggccgtcgtt  1200
```

-continued

```
gccccaggta tcgccgaagc gctgctggcc actgctctgg gcctggtcgc ggcaatcccg      1260
gccgtggtca tctacaacgt cttcgcccgc tccattgccg gttacaaggc acaggtgtcc      1320
gatgcctccg ctcaggtact gctgctggtc agccgtgatc tggaccacca gggtagcgag      1380
cgcgccgccc cgcacatggt gaaagtgggg taagccatgg gcctgcatct caacgaaggt      1440
ggcgacgacc tcgccgaaaa ccacgaaatc aacgttacgc cgttcatcga cgtgatgctg      1500
gtgctgctga tcatcttcat ggtcgccgcc cccttggcca cggtcgacat caaggtcgac      1560
ctgccggcct caaccgccaa accggcgcca aggccagaga aaccggtgtt cgttagcgtc      1620
aaggccgacc agaagctgta tgtcggcgac gatcaggttg ctgcacccga ccagcttggc      1680
ccgatgctcg acgccaagac caagggtgac aaggaaacca ccatcttctt ccaggctgac      1740
aaaggcgtgg attacggcga cctgatggag gtgatgaaca catgcgcgc ggccggctac      1800 ctgaaagtcg gtctggtagg tctcgagacg gcagccaaga aatgatgaaa acgcgctcta      1860
acatggcgcg ctacggtggc agcctggcga tcgtgctggg tgtgcacgtg gtcgccgtgc      1920
tgctgacgct caactggtcg gtaccacagg ccatcgaact gccccggca gcgatgatgg      1980 tcgaactggc accgttgccg gagcctgcgc caccaccacc cccaaaggca gctccgcagc      2040
caccggcacc ggtcgaggaa ccaccgttgc cgaagctggc agaagcgccc aagcccaaga      2100
tcgccatccc caagccgccc aagccaaagg ccaagccgca gccgcccaag cccgagaaaa      2160
agcctgagcc gccgaaggaa gcaccaccca ccgagcaaac ggtggacgca ccgcccagca      2220
acacgccacc gcagaagtcc gcggcaccgg caccaagcat tgcgtccaac agcaacgccc      2280
tgccaacctg gcagagcgac ctgctgcgcc accttgccaa gtacaagcgt tacccggaag      2340
acgcgcgccc tcgtggcctg caaggcatga accgcctgcg cttcgtggtc gacgccgaag      2400
gcaaggtcgt gtcgtactcc atggccggtg gctcgggcag tgccgcactg accgggcga       2460 ccctggaaat gatccgtcgg gccggcacgg tacccaagcc gccacccgag ttgctgaaca      2520
atggcacgat tgaagtcgtg gcaccgttcg tctactcact ggaccgccgc taagactttt      2580
gtttctgtca caattcggca agtctgataa cgtgcgtcta tcaat                     2625
```

<210> SEQ ID NO 2
<211> LENGTH: 963
<212> TYPE: DNA
<213> ORGANISM: Pseudomonas putida
<220> FEATURE:
<221> NAME/KEY: CDS
<222> LOCATION: (1)..(963)
<223> OTHER INFORMATION: exbB gene

<400> SEQUENCE: 2

```
atg aca cgt act caa cct tcc gct tcg cca acc ccg tcg cgc gcc tgg        48
Met Thr Arg Thr Gln Pro Ser Ala Ser Pro Thr Pro Ser Arg Ala Trp
1               5                   10                  15 cgc gcc atc gcc gcg ctg aca ctc agc ctg gtg ctg gcc ccg gtg gcc        96
Arg Ala Ile Ala Ala Leu Thr Leu Ser Leu Val Leu Ala Pro Val Ala
                20                  25                  30 atg gcc gat gag cca acc acc aac gcc gcc aca cct gcg gct gct act       144
Met Ala Asp Glu Pro Thr Thr Asn Ala Ala Thr Pro Ala Ala Ala Thr
            35                  40                  45 gcc ccg gcc gca ccc gct gct gcc ccg gtc gat gcg ccg gcg cct ggt       192
Ala Pro Ala Ala Pro Ala Ala Ala Pro Val Asp Ala Pro Ala Pro Gly
        50                  55                  60 gcc act gcc acc aac ccg gca gat gca gac cca agc gtt caa gcc ctg       240
Ala Thr Ala Thr Asn Pro Ala Asp Ala Asp Pro Ser Val Gln Ala Leu
```

-continued

```
                    65                  70                  75                  80
gtc gaa gac acc tcg ctg ggc atg gcc cat gac ctg tcc cca tgg ggc       288
Val Glu Asp Thr Ser Leu Gly Met Ala His Asp Leu Ser Pro Trp Gly
                85                  90                  95 atg tac aag aac gcc gac atc gtg gtg aag atc gtc atg atc ggt ctg       336
Met Tyr Lys Asn Ala Asp Ile Val Val Lys Ile Val Met Ile Gly Leu
            100                 105                 110 gcc atc gcc tcc atc atc acc tgg acc atc tgg att gcc aaa ggc ttc       384
Ala Ile Ala Ser Ile Ile Thr Trp Thr Ile Trp Ile Ala Lys Gly Phe
        115                 120                 125 gag ctg atg ggc gcc aag cgt cgc ctg cgg ggt gaa atc gcc cag ttg       432
Glu Leu Met Gly Ala Lys Arg Arg Leu Arg Gly Glu Ile Ala Gln Leu
    130                 135                 140 aag aag tcc acc acc ctg aag gaa gcc agc gaa gtc tcc aac aag gaa       480
Lys Lys Ser Thr Thr Leu Lys Glu Ala Ser Glu Val Ser Asn Lys Glu
145                 150                 155                 160 ggc acc ctg gcc cac acc ctg gtc cac gat gcc ctc gaa gag atg cgt       528
Gly Thr Leu Ala His Thr Leu Val His Asp Ala Leu Glu Glu Met Arg
                165                 170                 175 ctt tcg gct aac gct cgc gaa aaa gaa ggc atc aag gag cgc gtc agc       576
Leu Ser Ala Asn Ala Arg Glu Lys Glu Gly Ile Lys Glu Arg Val Ser
            180                 185                 190 ttc cgt ctg gag cgc ctg gtg cat gcc agc ggc cgc acc atg agc agc       624
Phe Arg Leu Glu Arg Leu Val His Ala Ser Gly Arg Thr Met Ser Ser
        195                 200                 205 ggc acc ggc gtc ctc gca acc atc ggc tcc acc gca ccg ttc gtt ggc       672
Gly Thr Gly Val Leu Ala Thr Ile Gly Ser Thr Ala Pro Phe Val Gly
    210                 215                 220 ctg ttc ggt acc gta tgg ggc atc atg aac agc ttc atc ggc atc gcc       720
Leu Phe Gly Thr Val Trp Gly Ile Met Asn Ser Phe Ile Gly Ile Ala
225                 230                 235                 240 aag acc cag acc acc aac ctg gcc gtc gtt gcc cca ggt atc gcc gaa       768
Lys Thr Gln Thr Thr Asn Leu Ala Val Val Ala Pro Gly Ile Ala Glu
                245                 250                 255 gcg ctg ctg gcc act gct ctg ggc ctg gtc gcg gca atc ccg gcc gtg       816
Ala Leu Leu Ala Thr Ala Leu Gly Leu Val Ala Ala Ile Pro Ala Val
            260                 265                 270 gtc atc tac aac gtc ttc gcc cgc tcc att gcc ggt tac aag gca cag       864
Val Ile Tyr Asn Val Phe Ala Arg Ser Ile Ala Gly Tyr Lys Ala Gln
        275                 280                 285 gtg tcc gat gcc tcc gct cag gta ctg ctg ctg gtc agc cgt gat ctg       912
Val Ser Asp Ala Ser Ala Gln Val Leu Leu Leu Val Ser Arg Asp Leu
    290                 295                 300 gac cac cag ggt agc gag cgc gcc gcc ccg cac atg gtg aaa gtg ggg       960
Asp His Gln Gly Ser Glu Arg Ala Ala Pro His Met Val Lys Val Gly
305                 310                 315                 320 taa                                                                    963
```

<210> SEQ ID NO 3
<211> LENGTH: 320
<212> TYPE: PRT
<213> ORGANISM: Pseudomonas putida

<400> SEQUENCE: 3

```
Met Thr Arg Thr Gln Pro Ser Ala Ser Pro Thr Pro Ser Arg Ala Trp
1               5                   10                  15

Arg Ala Ile Ala Ala Leu Thr Leu Ser Leu Val Leu Ala Pro Val Ala
            20                  25                  30

Met Ala Asp Glu Pro Thr Thr Asn Ala Ala Thr Pro Ala Ala Ala Thr
```

-continued

```
                35                  40                  45
Ala Pro Ala Ala Pro Ala Ala Pro Val Asp Ala Pro Gly
             50                  55                  60
Ala Thr Ala Thr Asn Pro Ala Asp Ala Asp Pro Ser Val Gln Ala Leu
 65                  70                  75                  80
Val Glu Asp Thr Ser Leu Gly Met Ala His Asp Leu Ser Pro Trp Gly
                 85                  90                  95
Met Tyr Lys Asn Ala Asp Ile Val Val Lys Ile Val Met Ile Gly Leu
                100                 105                 110
Ala Ile Ala Ser Ile Ile Thr Trp Thr Ile Trp Ile Ala Lys Gly Phe
            115                 120                 125
Glu Leu Met Gly Ala Lys Arg Arg Leu Arg Gly Glu Ile Ala Gln Leu
130                 135                 140
Lys Lys Ser Thr Thr Leu Lys Glu Ala Ser Glu Val Ser Asn Lys Glu
145                 150                 155                 160
Gly Thr Leu Ala His Thr Leu Val His Asp Ala Leu Glu Glu Met Arg
                165                 170                 175
Leu Ser Ala Asn Ala Arg Glu Lys Glu Gly Ile Lys Glu Arg Val Ser
            180                 185                 190
Phe Arg Leu Glu Arg Leu Val His Ala Ser Gly Arg Thr Met Ser Ser
        195                 200                 205
Gly Thr Gly Val Leu Ala Thr Ile Gly Ser Thr Ala Pro Phe Val Gly
    210                 215                 220
Leu Phe Gly Thr Val Trp Gly Ile Met Asn Ser Phe Ile Gly Ile Ala
225                 230                 235                 240
Lys Thr Gln Thr Thr Asn Leu Ala Val Val Ala Pro Gly Ile Ala Glu
                245                 250                 255
Ala Leu Leu Ala Thr Ala Leu Gly Leu Val Ala Ala Ile Pro Ala Val
            260                 265                 270
Val Ile Tyr Asn Val Phe Ala Arg Ser Ile Ala Gly Tyr Lys Ala Gln
        275                 280                 285
Val Ser Asp Ala Ser Ala Gln Val Leu Leu Val Ser Arg Asp Leu
    290                 295                 300
Asp His Gln Gly Ser Glu Arg Ala Ala Pro His Met Val Lys Val Gly
305                 310                 315                 320
```

<210> SEQ ID NO 4
<211> LENGTH: 429
<212> TYPE: DNA
<213> ORGANISM: Pseudomonas putida
<220> FEATURE:
<221> NAME/KEY: CDS
<222> LOCATION: (1)..(429)
<223> OTHER INFORMATION: exbD gene

<400> SEQUENCE: 4

```
atg ggc ctg cat ctc aac gaa ggt ggc gac gac ctc gcc gaa aac cac        48
Met Gly Leu His Leu Asn Glu Gly Gly Asp Asp Leu Ala Glu Asn His
 1               5                  10                  15 gaa atc aac gtt acg ccg ttc atc gac gtg atg ctg gtg ctg ctg atc        96
Glu Ile Asn Val Thr Pro Phe Ile Asp Val Met Leu Val Leu Leu Ile
             20                  25                  30 atc ttc atg gtc gcc gcc ccc ttg gcc acg gtc gac atc aag gtc gac       144
Ile Phe Met Val Ala Ala Pro Leu Ala Thr Val Asp Ile Lys Val Asp
         35                  40                  45 ctg ccg gcc tca acc gcc aaa ccg gcg cca agg cca gag aaa ccg gtg       192
Leu Pro Ala Ser Thr Ala Lys Pro Ala Pro Arg Pro Glu Lys Pro Val
```

```
                50                  55                  60
ttc gtt agc gtc aag gcc gac cag aag ctg tat gtc ggc gac gat cag      240
Phe Val Ser Val Lys Ala Asp Gln Lys Leu Tyr Val Gly Asp Asp Gln
 65                  70                  75                  80 gtt gct gca ccc gac cag ctt ggc ccg atg ctc gac gcc aag acc aag      288
Val Ala Ala Pro Asp Gln Leu Gly Pro Met Leu Asp Ala Lys Thr Lys
             85                  90                  95 ggt gac aag gaa acc acc atc ttc ttc cag gct gac aaa ggc gtg gat      336
Gly Asp Lys Glu Thr Thr Ile Phe Phe Gln Ala Asp Lys Gly Val Asp
        100                 105                 110 tac ggc gac ctg atg gag gtg atg aac aac atg cgc gcg gcc ggc tac      384
Tyr Gly Asp Leu Met Glu Val Met Asn Asn Met Arg Ala Ala Gly Tyr
    115                 120                 125 ctg aaa gtc ggt ctg gta ggt ctc gag acg gca gcc aag aaa tga          429
Leu Lys Val Gly Leu Val Gly Leu Glu Thr Ala Ala Lys Lys
130                 135                 140
```

<210> SEQ ID NO 5
<211> LENGTH: 142
<212> TYPE: PRT
<213> ORGANISM: Pseudomonas putida

<400> SEQUENCE: 5

Met Gly Leu His Leu Asn Glu Gly Gly Asp Asp Leu Ala Glu Asn His
 1               5                  10                  15

Glu Ile Asn Val Thr Pro Phe Ile Asp Val Met Leu Val Leu Leu Ile
            20                  25                  30

Ile Phe Met Val Ala Ala Pro Leu Ala Thr Val Asp Ile Lys Val Asp
        35                  40                  45

Leu Pro Ala Ser Thr Ala Lys Pro Ala Pro Arg Pro Glu Lys Pro Val
    50                  55                  60

Phe Val Ser Val Lys Ala Asp Gln Lys Leu Tyr Val Gly Asp Asp Gln
65                  70                  75                  80

Val Ala Ala Pro Asp Gln Leu Gly Pro Met Leu Asp Ala Lys Thr Lys
                85                  90                  95

Gly Asp Lys Glu Thr Thr Ile Phe Phe Gln Ala Asp Lys Gly Val Asp
            100                 105                 110

Tyr Gly Asp Leu Met Glu Val Met Asn Asn Met Arg Ala Ala Gly Tyr
        115                 120                 125

Leu Lys Val Gly Leu Val Gly Leu Glu Thr Ala Ala Lys Lys
    130                 135                 140

<210> SEQ ID NO 6
<211> LENGTH: 732
<212> TYPE: DNA
<213> ORGANISM: Pseudomonas putida
<220> FEATURE:
<221> NAME/KEY: CDS
<222> LOCATION: (1)..(732)
<223> OTHER INFORMATION: tonB gene

<400> SEQUENCE: 6

```
atg atg aaa acg cgc tct aac atg gcg cgc tac ggt ggc agc ctg gcg       48
Met Met Lys Thr Arg Ser Asn Met Ala Arg Tyr Gly Gly Ser Leu Ala
 1               5                  10                  15 atc gtg ctg ggt gtg cac gtg gtc gcc gtg ctg ctg acg ctc aac tgg       96
Ile Val Leu Gly Val His Val Val Ala Val Leu Leu Thr Leu Asn Trp
            20                  25                  30 tcg gta cca cag gcc atc gaa ctg ccc ccg gca gcg atg atg gtc gaa      144
Ser Val Pro Gln Ala Ile Glu Leu Pro Pro Ala Ala Met Met Val Glu
```

```
                 35                  40                  45
ctg gca ccg ttg ccg gag cct gcg cca cca ccc cca aag gca gct       192
Leu Ala Pro Leu Pro Glu Pro Ala Pro Pro Pro Pro Lys Ala Ala
 50                  55                  60 ccg cag cca ccg gca ccg gtc gag gaa cca ccg ttg ccg aag ctg gca   240
Pro Gln Pro Pro Ala Pro Val Glu Glu Pro Pro Leu Pro Lys Leu Ala
 65                  70                  75                  80 gaa gcg ccc aag ccc aag atc gcc atc ccc aag ccg ccc aag cca aag  288
Glu Ala Pro Lys Pro Lys Ile Ala Ile Pro Lys Pro Pro Lys Pro Lys
                 85                  90                  95 gcc aag ccg cag ccg ccc aag ccc gag aaa aag cct gag ccg ccg aag  336
Ala Lys Pro Gln Pro Pro Lys Pro Glu Lys Lys Pro Glu Pro Pro Lys
                100                 105                 110 gaa gca cca ccc acc gag caa acg gtg gac gca ccg ccc agc aac acg  384
Glu Ala Pro Pro Thr Glu Gln Thr Val Asp Ala Pro Pro Ser Asn Thr
                115                 120                 125 cca ccg cag aag tcc gcg gca ccg gca cca agc att gcg tcc aac agc  432
Pro Pro Gln Lys Ser Ala Ala Pro Ala Pro Ser Ile Ala Ser Asn Ser
130                 135                 140 aac gcc ctg cca acc tgg cag agc gac ctg ctg cgc cac ctt gcc aag  480
Asn Ala Leu Pro Thr Trp Gln Ser Asp Leu Leu Arg His Leu Ala Lys
145                 150                 155                 160 tac aag cgt tac ccg gaa gac gcg cgc cgt cgt ggc ctg caa ggc atg  528
Tyr Lys Arg Tyr Pro Glu Asp Ala Arg Arg Arg Gly Leu Gln Gly Met
                165                 170                 175 aac cgc ctg cgc ttc gtg gtc gac gcc gaa ggc aag gtc gtg tcg tac  576
Asn Arg Leu Arg Phe Val Val Asp Ala Glu Gly Lys Val Val Ser Tyr
                180                 185                 190 tcc atg gcc ggt ggc tcg ggc agt gcc gca ctg gac cgg gcg acc ctg  624
Ser Met Ala Gly Gly Ser Gly Ser Ala Ala Leu Asp Arg Ala Thr Leu
                195                 200                 205 gaa atg atc cgt cgg gcc ggc acg gta ccc aag ccg cca ccc gag ttg  672
Glu Met Ile Arg Arg Ala Gly Thr Val Pro Lys Pro Pro Pro Glu Leu
210                 215                 220 ctg aac aat ggc acg att gaa gtc gtg gca ccg ttc gtc tac tca ctg  720
Leu Asn Asn Gly Thr Ile Glu Val Val Ala Pro Phe Val Tyr Ser Leu
225                 230                 235                 240 gac cgc cgc taa                                                   732
Asp Arg Arg <210> SEQ ID NO 7
<211> LENGTH: 243
<212> TYPE: PRT
<213> ORGANISM: Pseudomonas putida

<400> SEQUENCE: 7

Met Met Lys Thr Arg Ser Asn Met Ala Arg Tyr Gly Gly Ser Leu Ala
 1               5                  10                  15

Ile Val Leu Gly Val His Val Val Ala Val Leu Leu Thr Leu Asn Trp
                 20                  25                  30

Ser Val Pro Gln Ala Ile Glu Leu Pro Pro Ala Ala Met Met Val Glu
                 35                  40                  45

Leu Ala Pro Leu Pro Glu Pro Ala Pro Pro Pro Pro Lys Ala Ala
 50                  55                  60

Pro Gln Pro Pro Ala Pro Val Glu Glu Pro Leu Pro Lys Leu Ala
 65                  70                  75                  80

Glu Ala Pro Lys Pro Lys Ile Ala Ile Pro Lys Pro Pro Lys Pro Lys
                 85                  90                  95
```

-continued

```
Ala Lys Pro Gln Pro Pro Lys Pro Glu Lys Lys Pro Glu Pro Pro Lys
            100                 105                 110
Glu Ala Pro Pro Thr Glu Gln Thr Val Asp Ala Pro Pro Ser Asn Thr
        115                 120                 125
Pro Pro Gln Lys Ser Ala Ala Pro Ala Pro Ser Ile Ala Ser Asn Ser
    130                 135                 140
Asn Ala Leu Pro Thr Trp Gln Ser Asp Leu Leu Arg His Leu Ala Lys
145                 150                 155                 160
Tyr Lys Arg Tyr Pro Glu Asp Ala Arg Arg Gly Leu Gln Gly Met
                165                 170                 175
Asn Arg Leu Arg Phe Val Val Asp Ala Glu Gly Lys Val Val Ser Tyr
            180                 185                 190
Ser Met Ala Gly Gly Ser Gly Ser Ala Ala Leu Asp Arg Ala Thr Leu
        195                 200                 205
Glu Met Ile Arg Arg Ala Gly Thr Val Pro Lys Pro Pro Pro Glu Leu
    210                 215                 220
Leu Asn Asn Gly Thr Ile Glu Val Val Ala Pro Phe Val Tyr Ser Leu
225                 230                 235                 240
Asp Arg Arg
```

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide primer

<400> SEQUENCE: 8
aaggcacagg tgtccgat                                            18

<210> SEQ ID NO 9
<211> LENGTH: 18
<212> TYPE: DNA
<213> ORGANISM: Artificial sequence
<220> FEATURE:
<223> OTHER INFORMATION: Synthetic oligonucleotide primer

<400> SEQUENCE: 9
cagcagcacc agcatcac                                            18

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide primer

<400> SEQUENCE: 10
gattacggcg acctgatg                                            18

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide primer

<400> SEQUENCE: 11
taccgaccag ttgagcgt                                            18

METHODS FOR PRODUCTION OF P-HYDROXYBENZOATE IN BACTERIA

CROSS-REFERENCE TO RELATED APPLICATIONS

The present application is a continuation of, and claims priority to, U.S. application Ser. No. 09/968,122, filed Oct. 1, 2001, now abandoned, which claims the benefit under 35 U.S.C. § 119(e) of U.S. provisional application Ser. No. 60/236,879 filed on Sep. 29, 2000, the disclosures of each of which are incorporated herein by reference in their entireties.

FIELD OF INVENTION

The present invention relates to the fields of molecular biology and microbiology. More specifically, this invention pertains to a novel gene cluster, tonB operon (exbB, exbD, tonB) and its role in tolerance to aromatic compounds, aromatic amino acids, p-hydroxybenzoic acid (pHBA), and bactericidal agents in bacteria. In addition, a method for screening and characterizing pHBA tolerance is provided. By these methods, some strains with particular tolerance to pHBA were identified. Also provided are methods for producing bacterial strains which are more sensitive or tolerant to a variety of chemical compounds.

BACKGROUND

Toxicity of aromatic compounds, antibiotics, organic solvents and bacteriocidic agents to microorganisms presents a major problem in the field of microbiology. In addition, tolerance to pHBA, antibiotics, aromatic compounds, parabenes and aromatic amino acids are of significant importance in various biotechnology areas such as biotransformation, biodegradation, food, pharmaceuticals, and cosmetics. Factors influencing tolerance appear to be varied and not always understood. Increasingly, attention has turned to genetic manipulation to create microbes that are able to thrive in high concentrations of aromatic compounds and organic solvents or to create microbes that are more sensitive to antibiotics and bacteriocidic agents, e.g., parabene preservatives. Among these are microbes that can synthesize monomers that can be used for the ulterior synthesis of added value polymers. One of these products of interest is pHBA that can be synthesized from toluene as described below. para-Hydroxybenzoic acid (pHBA) is a key monomer for production of liquid crystal polymers, (e.g., Zenite® that are used in board displays of computers and other electronic devices and for parabene preservatives).

A current limitation on the biotransformation of toluene into pHBA is the relative toxicity of these compounds for cells (Sikema et al., *Microbiol. Rev.* 50:201-222 (1995), as well as the toxicity of the product being produced (WO 9856920). One enzymatic pathway of increasing commercial interest for biotransformation is that of toluene degradation through the toluene monooxygenase pathway (TMO pathway). This pathway includes the following steps: toluene is oxidized to p-cresol with toluene monooxygenase, p-cresol is progressively oxidized to p-hydroxybenzyl alcohol and p-hydroxybenzaldehyde with p-cresol methylhydroxylase, and p-hydroxybenzaldehyde is then oxidized to p-hydroxybenzoic acid (PHBA) with p-hydroxybenzaldehyde dehydrogenase and pHBA is further oxidized to protocatechuic acid (PCA) with p-hydroxybenzoate hydroxylase. PCA is further metabolized to the TCA cycle where it is used for cell biosynthesis or energy metabolism.

Bacteria that possess the TMO pathway are useful for the degradation of toluene and other organics and are able to use these as their sole source of carbon (Wright et al., *Appl. Environ. Microbiol.* 60:235-242 (1994); Duetz et al., *Appl. Environ. Microbiol.* 60:2858-2863 (1994); Leahy et al., *Appl. Environ. Microbiol.* 62:825-833 (1996)). Bacteria that possess the TMO pathway are common among the genus *Pseudomonas* and species known to possess it include *Pseudomonas putida, Pseudomonas fluorescens, Pseudomonas aeruginosa,* and *Pseudomonas mendocina*.

Recently, various strains of *Pseudomonas* possessing the TMO pathway have been used to produce muconic acid from toluene via manipulation of growth conditions (U.S. Pat. No. 4,657,863; U.S. Pat. No. 4,968,612). Additionally, strains of *Enterobacter* with the ability to convert p-cresol to p-hydroxybenzoic acid (PHBA) have been isolated from soil (JP 05328981). Further, JP 05336980 and JP 05336979 disclose isolated strains of *Pseudomonas putida* with the ability to produce pHBA from p-cresol.

Amaratunga et al., (U.S. Pat. No. 6,030,819) reported a method for fermentation of glucose to PHBA through the shikimic acid pathway using genetically engineered *E. coli.* These workers provided a plasmid which controls the overexpression of chorismate pyruvate lyase, the bacterial enzyme which catalyzes the production of pHBA from chorismate. The yield reported, concentration and time were 0.04 g pHBA per g glucose, 6.2 g/L and 40 hr, respectively. These values do not make this process very attractive.

Inactivation of pobA gene(s) that codes for p-hydroxybenzoate hydroxylase allow production of pHBA from toluene or p-cresol in microorganisms that posses the TMO pathway with complete conversion of these substrates to pHBA at high conversion yield and titer (WO 9856920). Inhibition of cell growth, pHBA production and the activity of the enzymes in the metabolic toluene degradation pathway in the presence of high concentrations of pHBA has been known for many years (Eklund T., *Int. J. of Food Microbiol.* 2, 159-167 (1985)). A fermentation method for the biological production of pHBA has-been developed (WO 9856920). However, the successful production of pHBA to high concentrations requires increasing the tolerance to pHBA.

Overexpression of an efflux system or its expression from a plasmid vector results in increased resistance of bacteria to a variety of toxic substances, while inactivation of an efflux system causes an increase in sensitivity to antibiotics and toxic substances (Li et al., *J. Bacteriol.* 180:2987-2991 (1998); Ramos et al., *J. Bacteriol.* 180:3323-3329 (1998)). Such efflux systems are increasingly being recognized in a wide range of bacteria, particularly gram-negative ones.

TonB-dependent energy transduction can be considered an all-purpose system for the delivery of energy to the outer membrane. This system is widely distributed among gram-negative bacteria (see list below), where it also energizes the transport of iron-siderophores and vitamin $B_{12}$ (Jarosik et al., *Infect. Immun.* 62:2470-2477 (1994); Torres et al., *Mol. Microbiol.* 23:825-833 (1997)). The TonB-dependent energy transduction complex consists of, at least, three proteins, TonB, ExbB, and ExbD. Although ExbB and ExbD are essential for TonB activity, TonB functions as the true energy transducer that couples the proton motive force of the cytoplasmic membrane to drive active transport at the outer membrane (Karlsson et al., *Mol. Microbiol.* 8:379-388 (1993); Braun, *FEMS Microbiol. Rev.* 16:295-307 (1995); Letain et al., *Mol. Microbiol.* 24:271-283 (1997); Kadner, Mol. Microbiol. 4:2027-2033 (1990); Postle, J. *Bioenerget. Biomemb.* 25:591-601 (1993); Moeck et al., *Mol. Microbiol.* 28:675-681 (1998)).

| Microorganisms Containing exbB, exbD and tonB Genes |
|---|
| *Aquifex aeolicus* |
| *Bordetella bronchiseptica* |
| *Campylobacter coli* |
| *Chlamydia pneumoniae* |
| *Chlamydia trachomatis* |
| *Enterobacter aerogenes* |
| *Escherichia coli* K-12 |
| *Escherichia coli* MG 1655 |
| *Haemophilus ducreyi* |
| *Haemophilus influenzae* |
| *Helicobacter pylori* 26695 |
| *Helicobacter pylori* J99 |
| *Klebsiella pneumoniae* |
| *Neisseria gonorrhoeae* |
| *Neisseria meningitidis* |
| *Pasteurella haemolytica* |
| *Pseudomonas aeruginosa* |
| *Pseudomonas putida* DOT-T1E |
| *Pseudomonas putida* WCS358 |
| *Salmonella typhimurium* |
| *Serratia marcenscens* |
| *Vibrio cholerae* |
| *Xanthomonas campestris* |
| *Yersinia enterolitica* |

While tonB genes and organization of the exbB and exbD, and tonB genes have been identified and characterized in a number of microorganisms, no prior art has been found which describes that tonB genes are involved in tolerance to a wide variety of chemicals such as pHBA, antibiotics, aromatic compounds, parabenes, and aromatic amino acids. Moreover, no prior work has disclosed that tonB mutants are sensitive to the above chemicals. It has previously been disclosed that tolerance to aromatic hydrocarbons involves the operation of the efflux pumps that remove toxic compounds from the membranes (Ramos et al., *J. Bacteriol.* 180:3323-3329 (1998) and Mosqueda et al., *Gene* 232:69-76 (1999)).

In summary, the current methods available to produce PHBA, aromatic compounds, antibiotics, aromatic amino acids, and bactericidal agents suffer from serious disadvantages which make their commercial production too expensive. Therefore, there remains a need to understand the mechanisms of tolerance in order to design better antibiotics, bacteriocidal and bacteriostatic agents, and to generate microbes with enhanced biocatalytic potential which can tolerate large amounts of the above mentioned compounds at a commercially reasonable cost. Moreover, there is a crucial need for controlling microbial tolerance to pHBA, aromatic compounds, antibiotics, aromatic amino acids, and bactericidal agents to allow their effective production, effective removal and further help to increase or decrease the effect of certain chemicals in a microbial cell growth.

SUMMARY OF THE INVENTION

The invention provides an isolated nucleic acid fragment of the tonB operon from *Pseudomonas* selected from the group consisting of: (a) an isolated nucleic acid fragment encoding all or a substantial portion of the amino acid sequence selected from the group consisting of SEQ ID NO:1; (b) an isolated nucleic acid fragment that is substantially similar to an isolated nucleic acid fragment encoding all or a substantial portion of the amino acid sequence selected from the group consisting of SEQ ID NO:1; (c) an isolated nucleic acid molecule that hybridizes with (a) under the following hybridization conditions: 6×SSC (1 M NaCl), 40 to 45% formamide, 1% SDS at 37° C., and a wash in 0.5× to 1×SSC at 55 to 60° C.; and (d) an isolated nucleic acid fragment that is complementary to (a), (b) or (c).

Specific embodiments include the isolated fragments of as set forth in SEQ ID NOs:1, 2, 4, 6, 8, 9, 10 or 11 wherein the nucleic acid fragment is isolated from a *Pseudomonas putida* DOT-T1E strain.

The invention also provides an isolated nucleic acid fragment encoding ExbB from *Pseudomonas* selected from the group consisting of: (a) an isolated nucleic acid fragment encoding all or a substantial portion of the amino acid sequence set forth in SEQ ID NO:3; (b) an isolated nucleic acid fragment that is substantially similar to an isolated nucleic acid fragment encoding all or a substantial portion of the amino acid sequence set forth in SEQ ID NO:3; (c) an isolated nucleic acid molecule that hybridizes with (a) under the following hybridization conditions: 6×SSC (1 M NaCl), 40 to 45% formamide, 1% SDS at 37° C., and a wash in 0.5× to 1×SSC at 55 to 60° C.; and (d) an isolated nucleic acid fragment that is complementary to (a), (b) or (c).

A further embodiment is an isolated nucleic acid fragment comprising 1) a first nucleotide sequence encoding a polypeptide of amino acids that has at least 90% identity based on Xnr BLAST algorithm, when compared to a polypeptide encoded by the *Pseudomonas putida* WCS ExbB gene (Ac. Number X70139), or 2) a second nucleotide sequence comprising the complement of the first nucleotide sequence.

Further, the invention includes a polypeptide encoded by any of the isolated nucleic acid fragments of this invention disclosed herein.

Also provided is an isolated nucleic acid fragment encoding exbD from *Pseudomonas* selected from the group consisting of: (a) an isolated nucleic acid fragment encoding all or a substantial portion of the amino acid sequence set forth in SEQ ID NO:5; (b) an isolated nucleic acid fragment that is substantially similar to an isolated nucleic acid fragment encoding all or a substantial portion of the amino acid sequence set forth in SEQ ID NO:5, (c) an isolated nucleic acid molecule that hybridizes with (a) under the following hybridization conditions: 6×SSC (1 M NaCl), 40 to 45% formamide, 1% SDS at 37° C., and a wash in 0.5× to 1×SSC at 55 to 60° C.; and (d) an isolated nucleic acid fragment that is complementary to (a), (b) or (c).

Further provided is an isolated nucleic acid fragment comprising 1) a first nucleotide sequence encoding a polypeptide of amino acids that has at least 97.9% identity based on Xnr BLAST algorithm when compared to a polypeptide encoded by the *Pseudomonas putida* WCS exbD gene (Ac. Number X70139) or 2) a second nucleotide sequence comprising the complement of the first nucleotide sequence.

Polypeptides encoded by any of the disclosed isolated nucleic acid fragments are part of this invention.

An isolated nucleic acid fragment encoding TonB from *Pseudomonas* selected from the group consisting of: (a) an isolated nucleic acid fragment encoding all or a substantial portion of the amino acid sequence set forth in SEQ ID NO:7; (b) an isolated nucleic acid fragment that is substantially similar to an isolated nucleic acid fragment encoding all or a substantial portion of the amino acid sequence set forth in SEQ ID NO:7; (c) an isolated nucleic acid molecule that hybridizes with (a) under the following hybridization conditions: 6×SSC (1 M NaCl), 40 to 45% formamide, 1%

SDS at 37° C., and a wash in 0.5× to 1×SSC at 55 to 60° C.; and (d) an isolated nucleic acid fragment that is complementary to (a), (b) or (c).

An isolated nucleic acid fragment comprising 1) a first nucleotide sequence encoding a polypeptide of amino acids that has at least 93.8% identity based on Xnr BLAST algorithm, when compared to a polypeptide encoded by the *Pseudomonas putida* WCS tonB gene (Ac. Number X70139), or 2) a second nucleotide sequence comprising the complement of the first nucleotide sequence.

Also provided are chimeric genes comprising the isolated nucleic acid fragment disclosed herein and operably linked to at least one suitable regulatory sequence.

Also provided are host bacterial cells transformed with any such chimeric gene disclosed herein.

Most preferably the invention includes the transformed host bacterial cell wherein the host bacterial cell is *E. coli, Pseudomonas* sp., *Pseudomonas mendocina*, or *Pseudomonas putida*.

A further embodiment is transformed host bacterial cell selected from the group consisting of (a) *Pseudomonas putida* EEZ10 (CECT 5311), and (b) *E. coli* (pPAT7) (CECT 5313).

Also provided is an isolated nucleic acid fragment selected from the group consisting of SEQ ID NO:8, SEQ ID NO:9, SEQ ID NO:10, and SEQ ID NO:1.

A method is provided to alter the expression level of *Pseudonmas* tonB proteins in a host bacterial cell, the method comprising: transforming a host bacterial cell with the chimeric gene of claim 16 or 22; and growing the transformed host bacterial cell produced under suitable conditions to express altered levels of *Pseudomonas* tonB operon gene relative to expression levels of an untransformed host bacterial cell.

A method is provided to produce PHBA comprising: culturing a *Psuedomonas* strain in a medium comprising an aromatic organic substrate, at least one suitable carbon source, and a nitrogen source, wherein the *Psuedomonas* strain comprises multiple copies of tonB operon genes relative to the number of copies of tonB operon genes of a non-transformed *Pseudonomas* strain; and recovering the pHBA produced in (a). More preferred is where this method uses the *Pseudomonas* strain selected from the group consisting of *Pseudomonas putida* EEZ10 (CECT 5311), *Pseudomonas mendocina* and *Pseudomonas putida* DOT-T1E (CECT 5312), *Pseudomonas putida* KT2400, *E. coli* ET8000, and *Acenitobacter calcoaceticus*. Highly preferred is where this method *Pseudomonas mendocina, Pseudomonas putida* DOT-T1E (CECT 5312), and *Pseudomonas putida* KT2440 are transformed with the plasmids pPAT7 or pPAT8. The method is further preferred wherein the aromatic organic substrate is selected from the group consisting of toluene, benzoic acid, p-hydroxybenzyl alcohol, p-hydroxybenzaldehyde, and p-cresol.

The method is also more preferred wherein the at least one suitable carbon source is selected from the group consisting of succinate, lactate acetate, ethanol, monosaccharides, oligosaccharides, and polysaccharides.

Additionally provided is a method to obtain a bacterial strain more sensitive than the parent strain to antibiotics, aromatic carboxylic, parabens, and aromatic amino acids comprising: (a) inactivating a TonB operon of a bacterial strain by suitable methods; (b) screening for tonB phenotypes; and (c) testing for sensitivity of the bacterial strain in agar plates or in liquid cultures. This method is more preferred wherein in step (a) above a TonB operon is inactivated by inserting a phoA gene into the genome of the bacterial strain. In this method the antibiotics comprise tetracycline, cefotaxime, imipenen, norfloxacine and ciproloxacine, and analogues thereof; the aromatic carboxylic acids comprise o-, m-, and p-methoxybenzoate, p-methylbenzoate, and p-chlorobenzoate, o-, m-, and p-aminobenzoate, toluene, and analogues thereof; the amino aromatic acids comprise L-tryptophan, L-histidine, L-tyrosine, and the parabenes comprise methylparabene and ethylparabenes and analogues thereof.

Also provided is a method to obtain a transformed bacterial strain that is more tolerant to pHBA and aromatic amino acids than an un-transformed host bacterial strain, comprising: (a) transforming an untransformed host bacterial strain with a tonB operon or a tonB gene; (b) screening the transformed host bacterial strain produced in (a) for tolerance to pHBA or aromatic amino acids greater than that of the untransformed host bacterial strain. Preferably, the host bacterial cell is *Pseudomonas* mendocina or *Pseudomonas putida*. Also preferably, in step (a) (transforming the untransformed host bacterial strain) is accomplished using plasmids pPAT7 or pPAT8.

BRIEF DESCRIPTION OF THE DRAWINGS AND SEQUENCE DESCRIPTIONS AND BIOLOGICAL DEPOSITS

The invention can be more fully understood from the following detailed description and the accompanying figures, biological deposits, and sequence descriptions, which form a part of this application.

FIG. 1 depicts the scheme of pPAT5. pPAT5 carries an approximate 5.7 kb SphI fragment of the chromosome of the PhoA5 mutant which contains the Km-resistant determinant of the mini-Tn5 used for mutagenesis and the chromosomal DNA fragment carrying exbD and tonB. pUC18 is referenced in Yannish-Perron et al., *Gene* 33:102 (1985).

Figure 2:
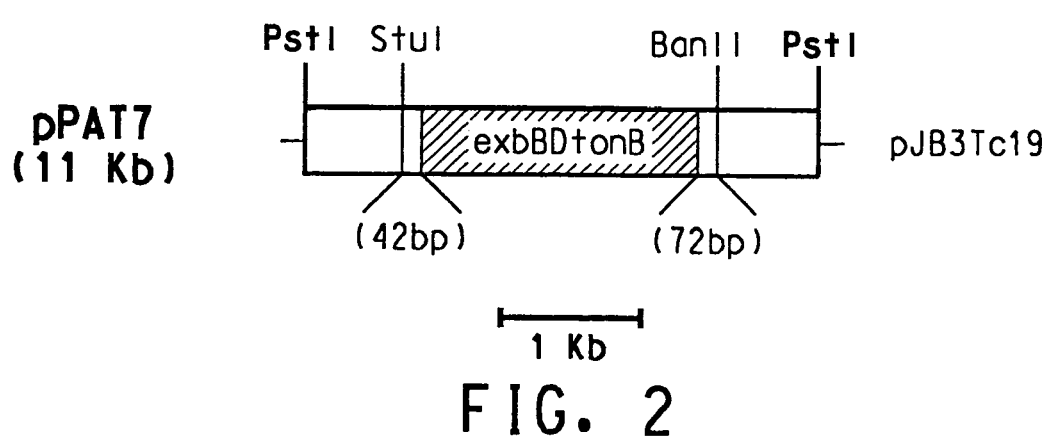

FIG. 2 depicts the scheme for plasmid pPAT7. pJB3-Tc19 is a derivative of pJB3 in which the TcR gene from pUC7Tc was inserted as a 2.3-kb BamHI fragment into the BglII sites. pJB3 is described in Blatny et al., *Appl. Environ. Microbiol.* 63:370-379 (1997). The b-lactamase gene in pJB3 was replaced with the Tc-resistant gene. pUC7Tc is a derivative of pUC7 in which the TcR gene of RK2 was cloned as a 2.3-kb blunt-ended StuI/BglII fragment into the HincII site of pUC7. pUC7 is described in Vieira et al., *Gene* 19:259-268 (1982).

Figure 3:
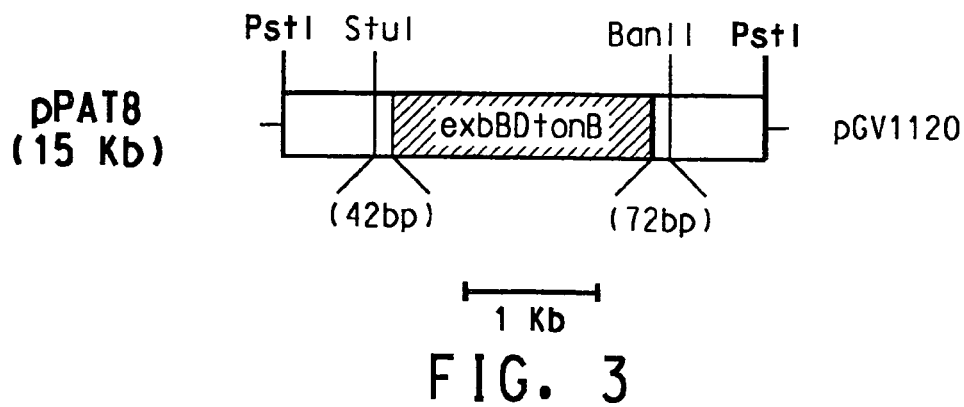

FIG. 3 depicts the scheme for plasmid pPAT8. The construction of pGV1120 is described Leemans et al., derived from the W-pasmid sa. *Gene* 19 (3):361-364 (1982).

Figure 4:
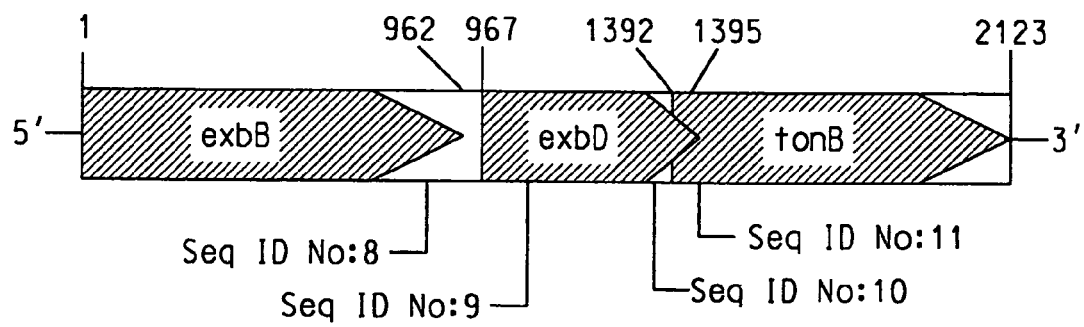

FIG. 4 depicts the organization of the exbB, exbD, and tonB genes of *P. putida* DOT-T1 E and the oligo primers used in RT-PCR assays to determine whether the genes form an operon. The results are described in Example 7. Applicants made the following biological deposits under the terms of the Budapest Treaty on the International Recognition of the Deposit of Micro-organisms for the Purposes of Patent Procedure at Colección Española de Cultivos Tipo (CECT) The Department of Microbiology, Faculty of Biology, 50 Dr. Moliner, 46100 Burjasot, Valencia, Spain. The "international Depository Designation" is the accession number to the materials deposited with the CECT.

| Depositor Identification Reference | International Depository Designation | Date of Deposit |
|---|---|---|
| *Pseudomonas putida* EEZ10 | CECT 5311 | 7 APR. 2000 |
| *Pseudomonas putida* DOT-T1E | CECT 5312 | 7 APR. 2000 |
| *E. coli* (pPAT7) (containing exbB, exbD, and tonB genes from *P. putida* DOT-T1E | CECT 5313 | 7 APR. 2000 |

Strain *P. putida* KT2440 is in the public domain and strain *P. putida* DOT-T1E was previously deposited (CECT4501) 13 Jun. 1994.

The deposits will be maintained in the indicated international depository for at least 30 years and will be made available to the public upon the grant of a patent disclosing it. The availability of a deposit does not constitute a license to practice the subject invention in derogation of patent rights granted by government action.

Applicant(s) have provided 11 sequences in conformity with 37C.F.R 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST. 25 (1998) and the sequence listing requirements of the EPO and PCT (Rules 5.2 and 49.5(a-bis), and Section 208 and Annex C of the Administrative Instructions).

SEQ ID NO:1 is the nucleotide sequence of the exbB, exbD, tonB gene cluster of *Pseudomonas putida* DOT-T1E. The start codons of exbB and exbD and tonB were located at positions 451-453, 1417-1419, and 1842-1844, respectively. The stop codons of exbB, exbD, and tonB were located at positions 1411-1413, 1843-1845, and 2571-2573, respectively.

SEQ ID NO:2 is the nucleotide sequence of the exbB gene which is a novel putative gene located in the chromosome of *P. putida* DOT-T1E. The start codon of exbB was located at positions 1-3. The stop codon of exbB was located at positions 961-963.

SEQ ID NO:3 is the deduced amino acid sequence of ExbB protein encoded by putative exbB gene (SEQ ID:2).

SEQ ID NO:4 is the nucleotide sequence of the exbD gene which is a novel putative gene located in the chromosome of *P. putida* DOT-T1E. The start codon of exbD was located at positions 1-3. The stop codon of exbD was located at positions 507-509.

SEQ ID NO:5 is the deduced amino acid sequence of ExbD protein which is encoded by the putative exbD gene (SEQ ID NO:4).

SEQ ID NO:6 is the nucleotide sequence of the tonB gene which is a novel putative gene located in the chromosome of *P. putida* DOT-T1E. The start codon of exbB was located at positions 1-3. The stop codon of exbB was located at positions 75-752.

SEQ ID NO:7 is the deduced protein sequence encoded by the putative tonB gene (SEQ ID NO:6) of *P. putida* DOT-T1E.

SEQ ID NO:8 is the nucleotide sequence of the primer used for amplification of the mRNA of the exbB and exbD genes in RT-PCR reactions to show mRNA contiguity. The sequence corresponds to nucleotide 1306-1323 in SEQ NO:1.

SEQ ID NO:9 is the nucleotide sequence of the primer used for amplification of the mRNA of the exbB and exbD genes in RT-PCR reactions to show mRNA contiguity. The sequence corresponds to the complementary sequence between positions 1492 and 1509 in SEQ NO:1.

SEQ ID NO:10 is the nucleotide sequence of the primer used for amplification of the mRNA of the exbD and tonB genes in RT-PCR reactions to show mRNA contiguity. The sequence corresponds to nucleotides 1750-1767 in SEQ NO:1.

SEQ ID NO:11 is the nucleotide sequence of the primer used for amplification of the mRNA of the exbB and exbD genes in RT-PCR reactions to show mRNA contiguity. The sequence corresponds to the complementary sequence between positions 1926-1943 in SEQ NO:1.

DETAILED DESCRIPTION OF THE INVENTION

A novel gene cluster has been cloned and sequenced from *Pseudomonas putida* DOT-T1E. This gene cluster was identified as exbB, exbD, tonB transcription unit or operon. The strain *Pseudomonas putida* DOT-T1E phoA5 was produced by disruption of exbD gene. Cloning the exbB, exbD, tonB transcription unit into the plasmid pPAT7 and transferring this plasmid to the phoA5 strain increased tolerance to aromatic compounds, pHBA, toluene, antibiotics, aromatic amino acids, terpenes, terpenoids, and parabenes to the wild-type level are produced. It is further shown that the tonB operon product of *P. putida* DOT-T1E is unique in the tonB family and is involved in tolerance to many chemicals. Also provided are methods to efficiently control microbial proliferation by inactivation of the genes of the present invention or inhibition of the activity of their protein products. These methods are useful in the bioproduction of these compounds by increasing tolerance of production hosts to the compound.

In summary, applicants have:
1) discovered that the tonB system is involved in tolerance to a wide variety of chemicals, besides antibiotics, including but not limited to aromatic carboxylic acids, aromatic hydrocarbons, parabenes, and aromatic amino acids.
2) shown that tonB mutants are sensitive to a wide variety of chemicals, besides antibiotics, including but not limited to aromatic carboxylic acids, aromatic hydrocarbons, parabenes, and aromatic amino acids.
3) identified pHBA-tolerant strains (i.e., *Pseudomonas putida* DOT-T1E, *Pseudomonas putida* KT2440, *Acinetobacter calcoaceticus*, *Pseudomonas putida* EEZ10, *Escherichia coli* ET8000, *Pseudomonas putida* R1) as the most tolerant strains. These strains improved pHBA production by allowing the fermentation to continue to higher concentrations.
4) discovered that overexpression of the *Pseudomonas putida* tonB system in plasmids, pPAT7 and pPAT8 in *P. menodcina* increased its tolerance to pHBA.
5) developed methods for screening and characterization of pHBA tolerance in bacteria.

The following definitions are provided in order to aid in understanding the detailed description of the present invention.

"PCR" is the abbreviation for polymerase chain reaction.

"pHBA" is the abbreviation for p-hydroxybenzoic acid which is also known as p-hydroxybenzoate.

"$logP_{OW}$" is the abbreviation for the partition coefficient of a given compound in a mixture of octanol-water.

The term "kam" refers to a gene encoding kanamycin resistance.

The term "Km" refers to kanamycin.

The term "amp" refers to a gene encoding ampicillin resistance.

The term "strep" or "Sm" refers to a gene encoding streptomycin resistance.

The term "TC" refers to tetracycline.

The term "pobA" refers to a gene encoding the para-hydroxybenzoate hydroxylase enzyme.

The term "phoA" refers to a gene encoding alkaline phosphatase enzyme.

The terms "bacteriocidic" and "bacteriostatic agents" refer to chemicals that kill or inhibit bacterial growth.

The term "parabenes" refers to esters of pHBA in which the carboxyl group on carbon one is esterified with methanol, ethanol, propanol, butanol or derivatives.

The term "aromatic amino acids" refers to the natural amino acids L-histidine, L-tyrosine, L-tryptophan, L-phenylalanine, and proline.

"Aromatic carboxylic acids" refers to benzene derivatives and are defined to include chemical compounds with a skeleton of benzene ring $C_6H_6$ where the substitution on the aromatic ring is selected from but not limited to:

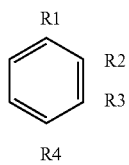

R1=carboxylic acid or corresponding salt (e.g., NH4+, K+, Na+) and where one of the R2, R3, and R4 is selected from the group consisting of methoxy, alkyl ($C_1$-$C_5$), alkenyl ($C_1$-$C_5$), amino, chloride, fluoride, bromide, iodine and the remaining substitutes are hydrogen. Specific examples of such aromatic carboxylic acids include toluene, para-cresol, benzaldehyde, and benzoic acid.

The term "Shine-Dalgarno sequence" refers to the *E. coli*'s ribosome binding site which has the consensus sequence of 5'-AGGAGGU-3'.

The terms "DOT-T1E-PhoA5" and "PhoA5" refer to *P. putida* DOT-T1E PhoA5 and are used interchangeably.

The term "ExbB protein" refers to the polypeptide that is encoded by the exbB gene.

The term "ExbD protein" refers to the polypeptide that is encoded by the exbD gene.

The term "TonB protein" refers to the polypeptide that is encoded by the tonB gene.

The terms "exbB, exbD, tonB operon", "exbB, exbD, tonB transcription unit", and "tonB operon" are used interchangably.

The term "aromatic organic substrate" refers to an aromatic compound that is degraded by the TMO enzymatic pathway. Examples of suitable aromatic substrates include, but are not limited to, toluene, p-hydroxylbenzyl alcohol, p-hydroxybenzaldehyde, and p-cresol.

The terms "tolerance" or "sensitivity" describe the ability to grow on specific medium agar plates or liquid medium in the presence of inhibitory compounds (e.g., antibiotics, aromatics, pHBA, toluene, organic solvents, preservatives, bacteriocidic and bacteriostatic agents, and aromatic amino acids).

The terms "host cell" and "host microorganism" refer to a cell capable of receiving foreign or heterologous genes.

The terms "recombinant organism", "transformed host", "transformant", and "transformed microbial host" refer to a microorganism having been transformed with heterologous or foreign genes.

The term "nucleic acid" refers to complex compounds of high molecular weight occurring in living cells, the fundamental units of which are nucleotides linked together with phosphate bridges. Nucleic acids are subdivided into two types: ribonucleic acid (RNA) and deoxyribonucleic acid (DNA).

The letters "A", "G", "T", and "C", when referred to in the context of nucleic acids, mean the purine bases (Adenine (C5H5N5) and Guanine (C5H5N5O)) and the pyrimidine bases (Thiamin (C5H6N2O2) and Cytosine (C4H5N3O)), respectively.

The term "nucleic acid fragment" refers to a fragment of DNA that may encode a gene and/or regulatory sequences preceding (5', upstream) or following (3', downstream) of the coding region (gene). A "fragment" constitutes a fraction of the complete nucleic acid sequence of a particular region. A fragment may constitute an entire gene.

The term "oligonucleotide" refers to primers, probes, oligomer fragments to be detected, labeled-replication blocking probes, and oligomer controls, and refers generically to polydeoxyribonucleotides (containing 2-deoxy-D-ribose), to polyribonucleotides (containing D-ribose) and to any polynucleotide which is an N glycoside of a purine or pyrimidine base (nucleotide), or modified purine or pyrimidine base. Also included in the definition of "oligonucleotide" are nucleic acid analogs and those that have been structurally modified (e.g., phosphorothioate linkages). There is no intended distinction between the length of a "nucleic acid", "polynucleotide", or an "oligonucleotide".

The term "primer" refers to an oligonucleotide (synthetic or occurring naturally), which acts as a point of initiation of nucleic acid synthesis or replication along a complementary strand when placed under conditions in which synthesis of a complementary strand is catalyzed by a polymerase.

The term "coding sequence" refers to a DNA sequence that codes for a specific amino acid sequence.

The term "suitable regulatory sequences" refer to nucleotide sequences that influence the transcription, RNA processing, RNA stability, or translation of the associated coding sequence and that are located upstream (5' noncoding sequences), within, or downstream (3' noncoding sequences) of a coding sequence.

The terms "peptide", "polypeptide", and "protein" are used interchangeably to refer to the gene product expressed.

The terms "ORF" and "open reading frame" are used interchangeably to refer to the portion of DNA sequence that translates into a protein. ORFs are usually delineated in the sequence by three base pairs designating the start (a start codon) and three base pairs designating the stop (a stop codon) in the translation of the DNA sequence into the protein sequence.

The terms "restriction endonuclease" and "restriction enzyme" refer to an enzyme which catalyzes hydrolytic cleavage within a specific nucleotide sequence in double-stranded DNA.

The term "probe" refers to an oligonucleotide (synthetic or occurring naturally), that is significantly complementary to a "fragment" and forms a duplexed structure by hybridization with at least one strand of the fragment.

The term "complementary" is used to describe the relationship between nucleotide bases that are hybridizable to one another. For example, with respect to DNA, adenosine is complementary to thiamin and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Codon degeneracy" refers to divergence in the genetic code permitting variation of the nucleotide sequence without affecting the amino acid sequence of an encoded polypeptide. Accordingly, the instant invention includes to any nucleic acid fragment that encodes all or a substantial portion of the amino acid sequence encoded by exbBexbDtonD gene cluster as set forth in SEQ ID NO:1.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines.

Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

"Suitable regulatory sequences" refer to nucleotide sequences located upstream (5' non-coding sequences), within, or downstream (3' non-coding sequences) of a coding sequence, and which influence the transcription, RNA processing, RNA stability, or translation of the associated coding sequence. Regulatory sequences may include promoters, translation leader sequences, and introns.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times or under most environmental conditions are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include sequences encoding regulatory signals capable of affecting mRNA processing or gene expression.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Mature" protein refers to a post-translationally processed polypeptide (i.e., one from which any pre- or propeptides present in the primary translation product have been removed).

"Precursor" protein refers to the primary product of translation of mRNA (i.e., with pre- and propeptides still present). Pre- and propeptides may be but are not limited to intracellular localization signals.

"Transformation" refers to the transfer of a DNA fragment into the genome of a host organism, resulting in genetically stable inheritance. Host organisms containing the transferred DNA fragments are referred to as "recombinant" or "transformed" organisms.

The term "gene cluster" refers to a set of genes that are adjacent to each other.

The term "operon" refers to genes that are transcribed into the same mRNA molecule.

The term "expression", as used herein, refers to the transcription and stable accumulation of sense (mRNA) derived from the nucleic acid fragment of the invention. Expression may also refer to translation of mRNA into a polypeptide or several polypeptides in the case of operons.

"Overexpression" refers to the production of a gene product in recombinant organisms that exceeds levels of production in normal or non-transformed organisms.

"Altered levels" refers to the production of gene product (s) in organisms in amounts or proportions that differ from that of normal, wild-type organisms.

The terms "plasmid" and "vector" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction. "Transformation cassette" refers to a specific fragment of DNA containing a set of genetic elements conveniently arranged for insertion into a host cell, usually as part of a plasmid. "Expression cassette" refers to a specific fragment of DNA containing a set of genetic elements conveniently arranged for insertion into a host cell, usually as part of a plasmid, that also allows for enhanced gene expression in the host.

The term "carbon source" refers to a substrate suitable for bacterial cell growth in the presence of nitrogen source and essential salts. Suitable carbon substrates include but are not limited to glucose, succinate, acetate, monosaccharides, oligosaccharides, or mixtures thereof.

The term "suicide vector" means a non-replicating vector that can be transferred to the host cell via conjugation or transformation, and it is a way to facilitate incorporation of foreign DNA to the bacterial chromosome. Examples of common suicide vectors and their construction may be found in Sambrook, J., Fritsch, E. F. and Maniatis, T. Molecular Cloning: A Laboratory Manual; Cold Spring Harbor Laboratory Press: Cold Spring Harbor, N.Y. (1989); Kaniga, K. et al., *Gene* 109:137-141 (1991); and de Lorenzo, V. et al., *J. Bacteriol.* 172:6568-6572 (1990)).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as substitution, deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically-equivalent amino acid at a given site, but do not affect the functional properties of the encoded protein are common. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Moreover, the skilled artisan recognizes that substantially similar nucleic acid sequences encompassed by this invention are also defined by their ability to hybridize, under stringent conditions, (0.1× SSC, 0.1% SDS, 65° C. and washed with 2×SSC, 0.1% SDS followed by 0.1×SSC, 0.1% SDS), with the sequences exemplified, herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule (such as a cDNA, genomic DNA, or RNA) when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T., *Molecular Cloning: A Laboratory Manual*, Second Edition, Cold Spring Harbor Laboratory Press, Cold Spring Harbor (1989), particularly Chapter 11 and Table 11.1 therein. The conditions of temperature and ionic strength determine the "stringency" of the hybridization.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved adding destabilizing agents such as formamide. Exemplary low stringency conditions include hybridization with a buffer solution of 6×SSC (1 M NaCl), 30 to 35% formamide, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 6×SSC (1 M NaCl), 40 to 45% formamide, 1% SDS at 37° C., and a wash in 0.5× to 1×SSC at 55 to 60° C. Exemplary high stringency conditions include hybridization in 6×SSC (1 M NaCl), 50% formamide, 1% SDS at 37° C., and a wash in 0.1×SSC at 60 to 65° C.

"Specificity" is typically a function of post-hybridization washes, the critical factors being the ionic strength and temperature of the final wash solution. The melting temperature ($T_m$) of a probe-target hybrid can be calculated to provide a starting point for the determining correct stringency conditions. For DNA-DNA hybrids, the $T_m$ can be approximated from the equation of Meinkoth and Wahl (*Anal. Biochem.*, (1984) 138:267-284: Tm=81.5° C.+16.6 (log M)+0.41 (% G+C)−0.61 (% form)−500/L; where M is the molarity of monovalent cations, % G+C is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, Laboratory Techniques in *Biochemistry and Molecular Biology—Hybridization with Nucleic Acid Probes*, Part I, Chapter 2 "Overview of principles of hybridization and the strategy of nucleic acid probe assays", (1993) Elsevier, New; and in *Current Protocols in Molecular Biology*, (1995) Chapter 2, Ausubel et al., Eds., Greene Publishing and Wiley-Interscience, New York.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art or by computer-automated sequence comparison and identification using algorithms such as BLAST (Basic Local Alignment Search Tool; Altschul et al., *J. Mol. Biol.* (1993) 215:403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequence encoding a bacterial protein. The skilled artisan, having the benefit of the sequence as reported herein, may now use all or a substantial portion of the disclosed sequence for purposes known to those skilled in this art. Accordingly, the instant invention comprises the complete sequence as reported in the accompanying Sequence Listing, as well as substantial portions of the sequence as defined above.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, N.J. (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Preferred computer program methods to determine identity and similarity between two sequences include, but are not limited to BLASTP, BLASTN, and FASTA (Pearson et al., *Proc. Natl. Acad. Sci.* U.S.A. (1988) 85:2444-2448, and Clustal W (Higgins et al., *Nucleic Acids Res.* 22:4673-4680). The BLAST X program is publicly available from NCBI and other sources (BLAST Manual, Altschul et al., *Natl. Cent. Biotechnol. Inf.*, Natl. Library Med. (NCBI NLM) NIH, Bethesda, Md. 20894; Altschul et al., *J. Mol. Biol.* (1990) 215:403-410). The Clustal W program is publicly available at http//dot.imgen.bcm.tmc.edu:9331/multialign/multialign.htm.

The nucleic acid fragments of the instant invention may be used to isolate cDNAs and genes encoding homologous enzymes from the same or other bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding similar proteins to that of the instant invention, either as cDNAs or genomic DNAs, could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full-length cDNA or genomic fragments under conditions of appropriate stringency.

Where PCR is used, two short segments of the instant ORFs may be used in polymerase chain reaction protocols to amplify longer nucleic acid fragments encoding homologous genes from DNA. The polymerase chain reaction may also be performed on a library of cloned nucleic acid fragments wherein the sequence of one primer is derived from the instant nucleic acid fragments.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33-50 IRL Press, Herndon, Va.), Rychlik, W. (1993) In White, B. A. (ed.), Methods in Molecular Biology, Vol. 15, pages 31-39, PCR Protocols: Current Methods and Applications. Humania Press, Inc., Totowa, N.J.)

Alternatively the instant sequences may be used as hybridization reagents for the identification of homologues. The basic-components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness et al., *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers, such as sodium citrate, Tris-HCl, PIPES or HEPES (pH range—about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kilodaltons), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, *Adv. Immunol.* 36:1 (1984).

The instant gene product may be produced in heterologous host cells. The preferred heterologous host cells for expression of the instant gene are microbial hosts. Particularly useful in the present invention will be cells that are readily adaptable to large-scale fermentation methods. Such organisms are well known in the art of industrial bioprocessing, examples of which may be found in "Recombinant Microbes for Industrial and Agricultural Applications", Murooka et al., eds., Marcel Dekker, Inc., New York, N.Y. (1994), and include fermentative bacteria. Host cells may include but not limited to the genera *Escherichia coli* and *Pseudomonas*. Microbial expression systems and expression vectors containing regulatory sequences that direct high level expression of foreign proteins are well known to those skilled in the art. Any of these could be used to construct chimeric genes for production of the gene products of the exbB, exbD tonB gene cluster. These chimeric genes could then be introduced into appropriate microorganisms via transformation to provide high level expression of the enzymes.

Additionally, chimeric genes will be effective in altering the properties of the host bacteria. It is expected, for example, that introduction of at least one copy of chimeric genes encoding the present ORFs under the control of the appropriate promoters into a host cell will demonstrate the ability to alter tolerance to a variety of aromatic compounds, pHBA, toluene, antibiotics, aromatic amino acids and parabene preservatives. Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a reg ion 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORFs in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $IP_L$, $IP_R$, T7, tac, $P_{BAD}$, and trc useful for expression in *Escherichia coli* and *Pseudomonas*.

Termination control regions may also be derived from various genes native to the preferred hosts. Optionally, a termination site may be unnecessary however; it is most preferred if included.

Optionally it may be desired to produce the instant gene cluster product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example EP 546049; WO 9324631). The secretion signal DNA may be between the expression-controlling DNA and the instant gene or gene fragment, and in reading frame with the latter.

Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction).

For example, putative exbB, exbD and tonB genes, as genomic DNAs, could be isolated directly by using all or a portion of the instant nucleic acid fragment as DNA hybridization probes to screen libraries from any desired microorganism employing methodology well known to those skilled in the art. Specific oligonucleotide probes based upon the instant putative exbB, exbD or tonB genes sequence can be designed and synthesized by methods known in the art. Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full-length genomic fragments under conditions of appropriate stringency.

In addition, two short segments of the instant nucleic acid fragment may be used in polymerase chain reaction protocols to amplify longer nucleic acid fragments encoding homologous putative exbB, exbD or tonB genes from DNA or RNA.

A plasmid vector comprising the instant chimeric gene can be constructed. The choice of plasmid vector is dependent upon the method that will be used to transfer it to the appropriate microorganisms. The skilled artisan is well aware of the genetic elements that must be present on the plasmid vector in order to successfully transform, select and propagate host cells containing the chimeric gene. By known methods the skilled artisan will screen clones displaying the desired expression level and pattern. For example, screening may be accomplished by Southern analysis of DNA, Northern analysis of mRNA expression, Western analysis of protein expression, or phenotypic analysis. Alternatively, mutants could be generated by various mutagenesis techniques and overexpressed and further screened or enriched for more tolerant strains, as described in detail in the instant invention.

The putative proteins produced in heterologous host cells, particularly in the cells of microbial hosts, can be used to prepare antibodies to the proteins by methods well known to those skilled in the art. The antibodies are useful for detecting the putative protein/s in situ in cells or in vitro in cell extracts. Preferred heterologous host cells for production of the putative protein are microbial hosts. Microbial expression systems and expression vectors containing regulatory sequences that direct high level expression of foreign proteins are well known to those skilled in the art. Any of these could be used to construct chimeric genes for production of the putative proteins. These chimeric genes could then be introduced into appropriate microorganisms via transformation to provide high level expression of putative proteins. Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

In addition to characterization of sensitivity to antibiotics and parabene preservatives which has broad implications in medicine and pharmaceutics, the present invention provides for increasing tolerance to toluene, pHBA, pHBA-related-products production and aromatics which is important in the field of biotechnology, and biotransformation in particular. Furthermore, the invention provides for sufficient information for overexpression of the exbB, exbD or tonB genes which may be accomplished by first constructing a chimeric plasmid in which the gene/s is/are expressed from a constitutive or regulatable promoter, so that expression can be achieved regardless of the growth conditions or in response to specific signal.

As exemplified herein, the present invention unexpectedly demonstrates that inactivation of tonB operon by genetic engineering methods as described here or by mutagenesis make the bacteria more sensitive to a variety of compounds, including toluene, pHBA, aromatic compounds, aromatic amino acids, antibiotics, and parabenes preservatives, and that overexpression of tonB operon can make them more tolerant to these compounds and thus accumulation of high concentration of pHBA would not be toxic and would not stop pHBA production.

In a specific embodiment, overexpression of the tonB operon in *P. mendocina* made the strain more tolerant to pHBA. It is further discovered that the tonB system is involved in tolerance to a wide variety of chemicals, besides antibiotics, including but not limited to aromatic carboxylic acids, aromatic hydrocarbons, parabenes and aromatic amino acids.

In another embodiment, a novel sequence of the exbB, exbD, tonB gene cluster of *Pseudomonas putida* DOT-T1E is provided. The present gene cluster was identified after comparison of the nucleic acid and deduced amino acid sequences to public databases using algorithms well known in the art. It was discovered that the ORFs were comprised of three stretches of 989, 428, and 732 bp which formed a single transcriptional unit. This gene cluster was needed for the growth of the strain on solid LB medium, and the strain has specific growth characteristics on various aromatic compounds, pHBA, toluene, antibiotics, and aromatic amino acids.

ORFs encoding the exbB, exbD, tonB gene cluster were identified by conducting BLAST (Basic Local Alignment Search Tool; Altschul, S. F., et al., (1993) *J. Mol. Biol.* 215:403-410; see also www.ncbi.nim.nih.gov/BLAST/) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The sequences obtained in Example 1 were analyzed for similarity to all publicly available DNA. sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266-272) provided by the NCBI. The results of the BLAST comparison is given in Table 1 which summarize the sequences to which they have the most similarity. Table 1 displays data based on the BLASTXnr algorithm with values reported in expect values. The Expect value estimates the statistical significance of the match, specifying the number of matches, with a given score, that are expected in a search of a database of this size absolutely by chance.

TABLE 1

| Gene Name | Similarity Identified | SEQ ID base | SEQ ID Peptide | % Identity[a] | E-value[b] | Citation |
| --- | --- | --- | --- | --- | --- | --- |
| exbB | exbB P. putida WCS 358 | 2 | 3 | 91 | 0 | Mol. Microbiol. 7:117-130 |
| exbD | exbD P. putida WCS 358 | 4 | 5 | 93 | e-180 | Mol. Microbiol. 7:117-130 |
| tonB | tonB P. putida WCS 358 | 6 | 7 | 88 | 0 | Mol. Microbiol. 7:117-130 |
| exbD | exbD E. coli K-12 | 4 | 5 | 88 | 3 × e-08 | Science 277:1453-1474 |
| exbB | exbB E. coli K-12 | 2 | 3 | 85 | 3 × e-16 | Science 277:1453-1474 |

[a]% Identity is defined as percentage of nucleotides that are identical between the two proteins.
[b]Expect value. The Expect value estimates the statistical significance of the match, specifying the number of matches, with a given score, that are expected in a search of a database of this size absolutely by chance.

Each newly defined ORF encodes an identifiable protein that is responsible for both intrinsic and acquired tolerance to a variety of aromatic compounds, pHBA, toluene, antibiotics, and aromatic amino acids. The sequences of the present invention were compared based on the *P. putida* tonB operon analysis against the "nr" database with those deposited at the GeneBank and a very high degree of sequence conservation was observed among the TonB proteins from different sources. The sequence comparison results are given below in Tables 2, 3, and 4 using Xnr BLAST algorithm.

It was found that the sequences of the present invention had greatest homology to the ExbB, ExbD, and TonB proteins of *Pseudomonas putida* WCS358 and to similar proteins of *E. coli*, *Pseudomonas aeruginosa*, *Helicobacter pylori*, and of other microorganisms. The tonB gene is not always linked to exbB and exbD homologues in some of the bacteria where they have been identified; however, the three genes appear to form an operon in several microorganisms including *P. putida*, *B. bronchiseptica*, *P. haemolytica*, *V. cholerae*, *N. meningitidis*, *N. gonorrhoeae*, *H. influenzae* Rd, and *H. ducreyi*. This is further illustrated in Tables 2, 3, and 4 where the degree of identity with the corresponding *P. putida* DOT-T1E proteins is shown. Genes with identity of less than 20% are not included.

TABLE 2

Degree of Identity of the ExbB Protein of *P. putida* DOT-T1E with the ExbB Proteins from other Microorganisms

| Strain | % identity[a] | Protein length | e-value[b] | Ac. number |
| --- | --- | --- | --- | --- |
| PP WCS358 | 90.0 | 329 | e-125 | X70139 |
| EC K-12 | 44.2 | 244 | 4e-58 | M28819 |
| PA | 23.1 | 239 | 7e-15 | AF190125 |
| BB | 28.9 | 314 | 3e-12 | AF087669 |
| ST | 40.0 | 110 | 5e-12 | P18950 |
| BP | 27.8 | 325 | 3e-12 | AJ132741 |
| NG | 22.5 | 220 | 1e-09 | U79563 |
| NM | 23.1 | 220 | 1e-09 | U77738 |
| XC | 25.3 | 253 | 3e-09 | Z95386 |
| CT | 20.8 | 232 | 0.011 | AE001330 |
| VC-1 | 20.6 | 228 | 0.095 | AF016580 |
| HP J99-1 | 20.0 | 189 | 6e-06 | AE001533 |
| HP 26695-1 | 19.7 | 189 | 4e-06 | AE000619 |

[a]% Identity is defined as percentage of amino acids that are identical between the two proteins.
[b]Expect value. The Expect value estimates the statistical significance of the match, specifying the number of matches, with a given score, that is expected in a search of a database of this size absolutely by chance.

Abbreviations are as follows: BB, *Bordetella bronchiseptica*; BP, *Bordetella pneumoniae*; EC K-12, *Escherichia coli*; HP, *Helicobacter pylori*; NG, *Neisseria gonorrhoeae*; NM, *Neisseria meningitidis*; PA, *Pseudomonas aeruginosa*; PPWCS 358, *Pseudomonas putida* WCS358; ST, *Salmonella thyphimurium*; VC, *Vibrio cholerae*; XC, *Xhantomonas campestris*; CT, *Chlamydia trachodermis*.

TABLE 3

Degree of Identity of the ExbD Protein of *P. putida* DOT-T1E with the ExbD Proteins from Other Microorganisms

| Strain | % identity | Protein length | e-value | Ac. number |
| --- | --- | --- | --- | --- |
| PPWCS | 97.9 | 142 | 4e-74 | X70139 |
| EC K-12 | 64.8 | 141 | 1e-45 | U28377 |
| PA | 35.2 | 133 | 8e-18 | AF190125 |
| NM | 34.5 | 144 | 8e-14 | U77738 |
| NG | 33.1 | 144 | 4e-13 | U79563 |
| HP J99-1 | 28.7 | 133 | 5e-12 | AE001533 |
| HP 26695-1 | 28.7 | 133 | 5e-12 | AE000619 |
| BB | 29.3 | 155 | 4e-11 | AF087669 |
| BP | 28.7 | 155 | 5e-11 | AJ132741 |
| XC-1 | 29.7 | 140 | 2e-10 | Z95386 |
| XC-2 | 27.2 | 136 | 5e-09 | Z95386 |
| AA | 25.9 | 132 | 2e-06 | AE000758 |
| HP J99-2 | 28.3 | 129 | 6e-06 | AE001549 |
| HP 26695-2 | 28.3 | 129 | 1e-05 | AE000635 |
| HI | 22.1 | 147 | 3e-05 | U08209 |
| HD | 24.3 | 129 | 1e-04 | AF001034 |
| PH | 23.8 | 145 | 3e-04 | U62565 |
| CP | 24.3 | 135 | 0.001 | AE001659 |
| CT | 20.8 | 135 | 0.011 | AE001330 |
| HP J99-3 | 22.8 | 133 | 0.033 | AE001556 |

Abbreviations are as in the footnote for Table 2, plus AA for *Aquifex aeolicus*; CP for *Chlamydia pneumoniae*; HD for *Haemophilus ducrey*, and HI for *Haemophilus influenzae*.

TABLE 4

Degree of Identity of the TonB Protein of *P. putida* DOT-T1E with the TonB Proteins from Other Microorganisms

| Strain | % identity | Protein length | e-value | Ac. number |
| --- | --- | --- | --- | --- |
| PPWCS358 | 93.8 | 243 | 1e-45 | X70139 |
| HP 26695 | 25.9 | 285 | 0.010 | AE000635 |
| HP J99-2 | 25.8 | 280 | 0.010 | AE001549 |
| PM | 30.2 | 256 | 0.20 | AF070473 |
| HI | 27.2 | 261 | 0.35 | U04996 |
| VC-1 | 24.5 | 244 | 0.45 | AF016580 |
| XC | 29.8 | 223 | 6.7 | Z95386 |

TABLE 4-continued

Degree of Identity of the TonB Protein of *P. putida* DOT-T1E with the TonB Proteins from Other Microorganisms

| Strain | % identity | Protein length | e-value | Ac. number |
|---|---|---|---|---|
| PA | 32.8 | 270 | 6.7 | AF190125 |
| PA-2 | 26.6 | 342 | 6.5 | U23764 |
| VP-1 | 21.8 | 247 | 8.8 | AF119047 |

Abbreviations are as in the footnote for Table 3.
PA refers to the tonB gene that forms part of the exbB, exbD, tonB cluster, while PA-2 refers to the second copy of the tonB gene that is unlinked to the previous cluster.

The results of Tables 2, 3, and 4 indicated that the protein sequence with the greatest homology to *P. putida* DOT-T1E ExbB protein was that of *P. putida* WCS358 (90% identical). The greatest homology to the *P. putida* DOT-T1E ExbD protein was that of *P. putida* WCS358 (98% identical). The sequence with the greatest homology to *P. putida* DOT-T1 E TonB protein was that of *P. putida* WCS358 (94% identical).

The preferred polypeptides of the instant invention are those active proteins which are at least 25% identical to the amino acid sequence reported herein. More preferred amino acid fragments are at least 54% identical to the sequences herein. Most preferred are amino acid fragments that are at least 75% identical to the amino acid fragments reported herein. Similarly, preferred nucleic acid sequences corresponding to the instant ORFs are those encoding active proteins and which are at least 25% identical to the nucleic acid sequences of reported herein. More preferred nucleic acid fragments are at least 54% identical to the sequences herein. Most preferred are nucleic acid fragments that are at least 75% identical to the nucleic acid fragments reported herein.

In yet another embodiment, the exbB, exbD, tonB gene cluster was rescued in a plasmid and transferred to the PhoA5 mutant strain. The transformed mutant strain recovered the ability to use pHBA as sole carbon source and the ability to tolerate toluene, pHBA, aromatic compounds, antibiotics, aromatic amino acids, and parabene preservatives to the tolerance level of the wild-type. Overexpression of this operon in *P. mendocina* made it more tolerant to pHBA and aromatic amino acids.

In addition to developing methods for screening and characterization of pHBA tolerance in bacteria, one embodiment of the present invention is the discovery that microorganisms differ widely in their ability to tolerate. PHBA. In this manner, strains with high tolerance to PHBA were identified, including *Pseudomonas putida* DOT-T1E (CECT 5312), *Pseudomonas putida* KT2440 (ATCC 47054), *Acinetobacter calcoaceticus, Pseudomonas putida* EEZ10 (CECT 5311). *Escherichia coli* ET8000 and *Pseudomonas putida* R1 were identified as very highly tolerant strains. These strains can improve pHBA production by allowing the fermentation to continue to higher concentrations.

In an alternate embodiment, the invention provides for a mutant strain which as a consequence of the insertion of the mini-Tn5-phoA in the exbD gene, was unable to grow on pHBA as the sole carbon source. Surprisingly, inactivation of the tonB operon rendered this strain more sensitive to a variety of chemical compounds such as toluene and pHBA.

Disruption or inactivation of tonB genes can be achieved as described below:

Mutagenesis with UV and gamma radiation, and chemical agents such as nitrosoguanidine and ethylmethanosulfonate (Ramos et al., *Proc. Natl. Acad. Sci.* 83:8467-8471 (1986)) have been commonly used in the past to generate punctual mutation in vivo. Transposons, transposable units with a selectable marker, are currently used as genetic tools to disrupt genes. Transposon mutagenesis may imply fusion to reporter genes (Manoil et al., *Science* 233:1403-1408 (1985)). The procedure of "random cloning" relies on random ligation of a selectable marker (i.e., an antibiotic resistance marker), to obtain restriction fragments of genomic DNA from the host; then recombination occurring during transformation promotes integration of the marker gene into the genome of the recipient cells (Chauvat et al., *Mol. Gen. Gen* 216:51-59 (1989)).

All the above mechanisms usefully generate random mutants that, followed by screening, permit the selection of those of interest. If specific gene inactivation is required, other methods in vitro are used, usually requiring cloning, gene inactivation, and further gene replacement by homologous recombination. To inactivate genes in vitro several methods are used: 1) transposition; 2) fusion to reporter genes (i.e. lux (Ramos-Gonzalez et al., *J. Bacteriol.* 180: 3421-3431 (1998)); 3) site-directed mutagenesis that permit altering the gene in target positions by using oligonucleotides with mismatches (feasible without previous cloning); 4) deletion combined with fusion to a reporter gene (i.e. xylE (Rodriguez-Herva et al., *J. Bacteriol.* 178:5836-5840 (1996)); 5) disruption by directed polar gene insertions, of special interest for inactivating polycistronic genes. Polar mutations are created with termination signals and interposons are the genetic tools normally used to generate them. An interposon ($\Omega$ fragment) consists of an antibiotic resistance gene flanked by inverted repeats carrying transcription and translation termination signals that is inserted into a linearized plasmid. The recombinant molecules are selected by their resistance to the antibiotic (Prentki et al., *Gene* 29:303-313 (1984)).

In a preferred embodiment, it was discovered that overexpression of the *Pseudomonas putida* tonB system in plasmids pPAT7 and pPAT 8 in *P. mendocina* increased its tolerance to pHBA and aromatic amino acids.

EXAMPLES

The present invention is further defined in the following Examples, in which all parts and percentages are by weight/volume and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

General Methods

Standard recombinant DNA and molecular cloning techniques used in the Examples are well known in the art and are described by Sambrook, J., Fritsch, E. F. and Maniatis, T. in Molecular Cloning: A Laboratory Manual; Cold Spring Harbor Laboratory Press: Cold Spring Harbor, N.Y. (1989) and by T. J. Silhavy, M. L. Bennan, and L. W. Enquist in Experiments with Gene Fusions, Cold Spring Harbor Laboratory, Cold Spring Harbor, N.Y. (1984) and by Ausubel, F. M. et al., Current Protocols in Molecular Biology, published by Greene Publishing Assoc. and Wiley-Interscience (1987).

The meaning of abbreviations is as follows: "h" means hour(s), "min" means minute(s), "seq" means second(s), "d" means day(s), "mL" means milliliters, "L" means liters, "Temp." means temperature, "mm" means millimeters, "M" means molar, "growth dist." means growth distribution, "Tol." means toluene Bacterial Strains

*Pseudomonas putida* DOT-T1E strain (Ramos et al., *J. Bacteriol.* 177:3911-3916 (1995)), *Pseudomonas putida* KT2440—ATCC 47054 (Franklin et al., *Proc Natl Acad Sci USA* 78:7458-7462 (1981)) and *Pseudomonas mendocina* Krc16 DK pobA51 (WO 9856920) were used as indicated in the following Examples.

TMO-Containing Bacterial Strains

Bacterial cells preferred in the present invention are those that possess the TMO pathway. Such strains are generally restricted to the genus *Pseudomonas* and may include *P. putida, P. fluorescens*, and *P. mendocina*.

Strains of *Pseudomonas* containing the TMO pathway are known to oxidize toluene to form intermediates of the tricarboxylic acid cycle. pHBA as well as other intermediates, such as p-cresol, p-hydroxybenzyl alcohol and p-hydroxybenzadehyde, are formed in the upper pathway, which metabolizes toluene to the ring cleavage substrate. In wild-type *Pseudomonas* strains, PHBA is immediately converted to protocatechuate (PCA) as it is formed. The biochemistry of the enzymes involved in the upper pathway have been described for several *Pseudomonas* strains.

Batch and Continuous Fermentations

The present process uses a batch method of fermentation. Classical batch fermentation is a closed system where the composition of the medium is set at the beginning of the fermentation and not subjected to artificial alterations during the fermentation. Thus, at the beginning of the fermentation the medium is inoculated with the desired organism or organisms and fermentation is permitted to occur adding nothing to the system. Typically, however, a batch fermentation is "batch" with respect to the addition of carbon source and attempts are often made at controlling factors such as pH and oxygen concentration. In batch systems the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the medium. An advantage of the Fed-Batch system is that it is more amenable to the use of toxic or immiscible aromatic substrates such as toluene. Using a Fed-Batch system it is possible to maintain a steady concentration of substrate at non-toxic levels while accommodating maximum bioconversion of the substrate to product.

The production of pHBA from aromatic compounds such as toluene will be limited by the amount of the aromatic substrate and carbon sources added. In simple Batch fermentation, production will be limited by the amount of toluene initially added. Since toluene is toxic and has limited solubility in water, its low initial concentration will govern the amount of pHBA produced. The ability to run the process at such a low toluene (i.e., 30-60 ppm) allows operation below a lower explosive limit which for toluene is 120 ppm. This is a clear safety advantage to the process. Fed-Batch techniques where the carbon source and toluene are added at rates which are similar to the utilization of these compounds will keep the toluene concentration in the medium low and can significantly increase the amount of PHBA produced.

Batch and fed-batch fermentations are common and well known in the art and examples may be found in, for example, Thomas D. Brock in Biotechnology: A Textbook of Industrial Microbiology, Second Edition (1989) Sinauer Associates, Inc., Sunderland, Mass., or Deshpande, Mukund V. *Appl. Biochem. Biotechnol.* 36, 227, (1992). Patent disclosure WO 9856920 describes fed and fed-batch methods for pHBA production.

It is contemplated that the method would be adaptable to continuous fermentation methods. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen source at low concentration and allow all other parameters to be in excess. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the fermentation. Methods of modulating nutrients and growth factors for continuous fermentation processes as well. as techniques for maximizing the rate of product formation are well known in the art of industrial microbiology and a variety of methods are detailed by Brock, supra.

It is contemplated that the present invention may be practiced using either batch, Fed-Batch or continuous processes and that any known mode of fermentation would be suitable. Additionally, it is contemplated that cells may be immobilized on a substrate as whole cell catalysts and subjected to fermentation conditions for pHBA production.

Fermentation Studies and Culture Conditions pHBA can be produced by genetically engineered *P. mendocina* or *P. putida* hosts having no p-hydroxybenzoate hydroxylase where all pobA genes are disrupted. The medium may optionally contain a nitrogen source, salts, carbon source and an aromatic substrate.

The culture medium can contain any inorganic or organic source of nitrogen normally used in processes for culturing microorganisms. Nitrogen sources may be either inorganic (ammonium salts, e.g., ammonium sulfate) or organic nitrogen (e.g., yeast extract).

In pobA(-) *P. mendocina* and *P. putida* cells, a carbon source is necessary as the TMO pathway is completely blocked, and the strain is not able to utilize the aromatic substrates as a carbon source for the production of energy. In practice, it is necessary to balance the concentration of the carbon substrate against the concentration of the aromatic carbon substrate in order to control the amount of oxidation of the aromatic substrate at the beginning of the TMO pathway.

A variety of carbon sources are suitable in the present invention and include but are not limited to materials such as succinate, lactate, acetate, ethanol, monosaccharides (such as glucose and fructose), oligosaccharides (such as lactose or sucrose), polysaccharides (such as starch or cellulose or mixtures thereof) and unpurified mixtures from renewable feedstocks (such as cheese whey permeate, cornsteep liquor, sugar beet molasses, and barley malt). The choice of the carbon substrate will be determined by the needs of the desired production cell. For the purposes of the present invention, glucose is preferred.

A variety of aromatic substrates may be used in the present invention, including but not limited to toluene, p-cresol, p-hydroxybenzyl alcohol, p-hydroxybenzaldehyde, benzoate and any aromatic compounds where the chemical structure is similar to toluene and the intermediates of the TMO pathway.

The production of pHBA from aromatic substrates such as toluene and p-cresol will be limited by the concentration of the substrate and the carbon source in the medium. Preferred concentrations of toluene are from about 30 ppm to about 500 ppm where a range of about 30 ppm to about 60 ppm is most preferred. Preferred concentrations of p-cresol are from about 1 mM to about 5 mM.

Growth Conditions

Typically, studies were conducted in flasks and 1 and 10-L fermentors and the fermentation modes used were batch, fed-batch and continuous. M9 minimal medium with micronutrients supplemented as described by Abril et al., (*J. Bacteriol.* 171:6782-6790 (1989)). Optionally a basal salts medium containing 0.48 g/L of yeast extract ("lean medium") or the same medium but with 4 g/L yeast extract and 10 g/L N-Z-amine E ("rich medium" Sheffield Products, Kraft Inc.) can be used. In the culture medium, glucose was the carbon source and ammonium was the inorganic nitrogen source.

Other media amenable to the procedures of the present invention are common in the art and are fully described in *Manual of Methods for General Bacteriology* ((Phillipp Gerhardt, R. G. E. Murray, Ralph N. Costilow, Eugene W. Nester, Willis A. Wood, Noel R. Krieg and G. Briggs Phillips, eds, American Society for Microbiology, Washington, D.C. (1994)).

It is preferred that the cells are cultured in a 2-phase process, where the cells are first grown to a suitable cell density in the first stage and then transferred to a production medium containing the aromatic carbon substrate for pHBA production in a second stage. Preferred cell densities for the first and second stage culture are from about 0.1 g/L to about 50 g/L.

Growth Evaluation

Growth is evaluated semi-quantitatively by the density of growth on plates, by the length of growth against the gradient of the growth inhibitory compound, by the size of colonies obtained after a specific time of incubation, or by the zone of growth inhibition obtained around filter paper disks impregnated with growth inhibitory compounds and placed in specific-medium agar plates (Haleo-inhibition test). Quantitative evaluation of growth inhibition by inhibitory compounds was by measuring culture turbidity over time by optical methods (e.g. turbidity at 600 nm or counting on plates for colony forming units (CFU)). Reduction of CFU after the addition of growth inhibitory compound(s) was another way to evaluate tolerance to growth inhibitory or toxic compounds.

Halo-Inhibition Test

The Halo-inhibition test was performed as follows: small filter paper disks impregnated with test compounds and were placed on media agar plates that were spread with a test organism. Then the plates were incubated to allow growth of the test organism and observed for inhibition zones around the disks. The bigger the inhibition zone surrounding the paper disks, the stronger the inhibition or killing capacity of the test compound (Sukupolyi, S. et al., *J. Bacteriol.* 159: 704-712 (1983)).

Mutagenesis Using Mini-Tn5-phoA

Manoil and Beckwith (*Proc. Natl. Acad. Sci. USA* 82:8129-8133 (1985)) demonstrated how protein fusions of the *Escherichia coli* alkaline phosphatase gene (phoA) could be used for analyzing synthesis of exported proteins and the topology of membrane proteins. Wild-type *Pseudomonas putida* strains contain a low level of alkaline phosphatase and are phenotypically PhoA-minus (colorless colonies) on plates containing 5-bromo-4-chloro-3-indolyl phosphate (BCIP). De Lorenzo et al., (*J. Bacteriol.* 172:6568-6572 (1990)) have constructed a mini-Tn5 transposon that bears a promoterless phoA gene lacking its signal peptide sequence and a kanamycin resistance. This transposon can be used to create in-frame fusions of exported proteins in *Pseudomonas* sp. (Rodriguez-Herva et al., *J. Bacteriol* 178:1699-1706 (1996)). Upon mutagenesis of *Pseudomonas putida* DOT-T1E, successful inactivation of a membrane protein can be selected because colonies are blue on plates with BCIP and kanamycin.

Example 1

Tolerance of *Pseudomonas putida* DOT-T1E to p-Hydroxybenzoate

This is the first example of a microbe growing in the presence of such high concentrations, of pHBA. The effect of p-hydroxybenzoate on the growth of *Pseudomonas putida* DOT-T1E was analyzed in M9 liquid culture medium. Thirty mL of M9 minimal medium with glucose and containing increasing concentrations of p-hydroxybenzoate were inoculated with 0.3 mL of an overnight culture of *Pseudomonas putida* DOT-T1E grown in the same culture medium with glucose as the sole carbon source. Growth was followed by determining the number of colony forming units (CFU) per mL of culture. The growth of *Pseudomonas putida* DOT-T1E with glucose in the absence and in the presence of p-hydroxybenzoate (PHBA) was investigated. With glucose alone or in the presence of 6 g/L of p-hydroxybenzoate growth was exponential. When the concentration of p-hydroxybenzoate reached 12 or higher g/L the number of viable cells decreased. However, growth resumed at 12 g/L pHBA upon prolonged incubation.

Example 2

Cumulative Effect of Preculture of *Pseudomonas putida* DOT-T1E on p-Hydroxybenzoate and 10 mM $MgSO_4$ This example shows that tolerance to pHBA in *P. putida* DOT-T1E can be increased by manipulating the chemical composition of the culture medium. To test whether preexposure of *Pseudomonas putida* DOT-T1E to a low concentration of p-hydroxybenzoate (6 g/L) had an effect on survival upon a shock of high concentrations of p-hydroxybenzoate (>12 g/L), the following test was performed. Bacterial cells were grown overnight at 30° C. in a rotary incubator on minimal culture medium with glucose (0.5% wt/v), in the presence or in the absence of 6 g/L pHBA. Cells were then diluted 100-fold in the same culture medium except that the concentration of PHBA was varied between 6 and 36 g/L and the culture medium contained either 1 or 10 mM $MgSO_4$. For cells not pregrown on pHBA, pHBA shocks (>18 g/L) resulted in a marked decrease in cell viability, regardless of the concentration of $MgSO_4$ in the culture medium. At concentrations of 30 and 36 g/L no cells were recovered 24 h after the shock. For preinduced cells, up to 0.18 g/L PHBA had no significant effect on cell viability regardless of the $MgSO_4$ concentration in the culture medium. At higher pHBA concentrations (i.e., 30 and 36 g/L pHBA) and when the concentration of $MgSO_4$ was 1 mM, viability was lost to such an extent that cells were not recoverable on plates 24 h after the shock. However, in the presence of 10 mM $MgSO_4$, there was some survival after a 30 g/L shock. It should be noted that although the number of viable cells decreased significantly (almost 6 orders of magnitude), growth resumed afterwards and a high cell density was reached. When the pHBA concentration was 36 g/L, the presence of 10 mM $MgSO_4$ did not prevent cell death.

Example 3

Selection of *Pseudomonas putida* DOT-T1E Clones with Altered Pattern of Sensitivity to pHBA This example shows that it is possible to modulate the tolerance/sensitivity to pHBA of *P. putida* DOT-T1E-through the modification of the culture medium composition. A bank of phoA mutants of *Pseudomonas putida* DOT-T1E was generated as follows: about $10^8$ cells of the parental strain *Pseudomonas putida* DOT-T1E ($Rif^R$) were mated with *E. coli* CC118 PIR(pUT-Km-phoA, pRK600). The $PhoA^+$, Km resistant *Pseudomonas putida* DOT-T1E transconjugants were selected as $Rif^R$, $Km^R$, and blue colonies ($PhoA^+$) on plates of M9 minimal medium with glucose as the sole carbon source (Abril, M. A. et al., *J. Bacteriol.* 171, 6782-6790 (1989)), 10 μg/mL Rif, 25 μg/mL Km, and 20 μg/mL of BCIP. About 200 $Km^R$, $PhoA^+$ mutants were tested for increased tolerance/sensitivity to pHBA on double diffusion solid M9 minimal medium with 0.5% (wt/vol) glucose and a pHBA gradient between 0 and 20 g/L. The wild-type and each of the two hundred clones were grown overnight on M9 minimal medium with glucose. One hundred μL were spread on plates and incubated for 20 h at 30° C., and growth was examined. One strain grew at a concentration of pHBA below 8 g/L, in contrast with the wild type, and rest of the mutants grew well up to about 15-17 g/L. The putative mutant clone was called DOT-T1E-PhoA5. To further corroborate that the mutant was more sensitive than the wild type to pHBA, DOT-T1E and DOT-T1E-PhoA5 were grown overnight on minimal medium with 0.5% (wt/vol) glucose as the sole carbon source, serial dilutions were then spread on plates with glucose supplemented with 0, 3, 6 or 9 g/L pHBA. The wild-type strain formed colonies in all plates, whereas the mutant strain produced colonies only on plates with less than 6 g/L pHBA. The response of DOT-T1E-PhoA5 to PHBA shocks was also analyzed. To this end wild-type and mutant cells were pregrown overnight on minimal medium with glucose, then diluted 50-fold in the same medium; 3 h later each culture was split into four aliquots to which 6, 9, 12 or 15 g/L pHBA was added. For the wild-type strain a high cell density ($\geq 10^9$ CFU/mL) was found in all cases after 50 h of incubation. At the two lowest concentrations growth was not initially inhibited, although it was severely inhibited after shock with the two highest concentrations. For the mutant strain all concentrations inhibited growth: the higher the pHBA concentration the larger the decrease was in cell viability.

Example 4

Physiological Characterization of a phoA Mutant with an Altered Pattern of Sensitivity to p-Hydroxybenzoate Antibiotic Resistance Pattern of the Wild-Type and DOT-T1E-PhoA5 Mutant in Minimal Medium:

The pattern of tolerance/sensitivity to different antibiotics of the mutant strain was tested on minimal medium using the Halo-inhibition test. Antibiotics were supplied on 6-mm disks impregnated with one of the following (μg): ampicillin (10), vancomycin (30), chloramphenicol (30), rifampicin (30), nalidixic acid (30), tetracycline (30), streptomycin (10), gentamycin (10), erythromycin (15), piperacillin (100), cefotaxime (30), imipenen (10), norfloxacine (10), and ciprofloxacine (5).

Both the wild-type and mutant strains were tolerant to ampicillin, vancomycin, erythromycin, chloramphenicol, and rifampicin. Both strains were equally sensitive to nalidixic acid, streptomycin, gentamycin and piperacillin. Although both strains were sensitive to tetracycline, cefotaxime, imipenen, norfloxacine, and ciprofloxacine, the inhibition halo produced by the mutant strain was larger than that produced by the wild-type one (Table 5).

TABLE 5

Pattern of Sensitivity to Antibiotics of *Pseudomonas putida* DOT-T1E and Mutant PhoA5

| Strain | NA | TE | SM | GM | PIP | CTX | IPM | NOR | CIP |
|---|---|---|---|---|---|---|---|---|---|
| PhoA5 | 15 | 28 | 14 | 16 | 19 | 30 | 45 | 30 | 40 |
| T1E | 15 | 21 | 16 | 17 | 18 | 14 | 26 | 20 | 21 |

The number indicates the size of the inhibition halo in mm.
Abbreviations: NA, nalidixic acid; TE, tetracycline; SM, streptomycin; GM, gentamycin; PIP, piperacillin; CTX, cefotaxime; IPM, imipenen; NOR, norfloxacine, and CIP, ciprofloxamine.

Utilization of Different Carbon-Sources by DOT-T1E and DOT-T1E-PhoA

Growth of the wild-type and the mutant strain was tested on minimal medium with different carbon sources. For this series of assays cells were grown overnight on M9 minimal medium with 5 g/L glucose. Then cultures were diluted 50-fold on M9 minimal medium with succinate (10 mM), citrate (10 mM), glycerol (1% wt/vol), p-hydroxybenzoate (5 g/L), glucose. (0.5% wt/vol) and toluene supplied via the gas phase as a carbon source. On liquid minimal medium both strains grew with similar doubling times with glucose, succinate, and glycol (Table 6). DOT-T1E grew significantly slower on citrate. The growth of PhoA5 was impaired on PHBA as the sole carbon source. In fact the strain seemed to be unable to grow on minimal medium with 1 to 5 g/L PHBA as the sole carbon source.

TABLE 6

Doubling time* of *Pseudomonas putida* DOT-T1E and DOT-T1E-PhoA5 on minimal medium with different carbon sources.

| Carbon Source | Strain: DOT-T1E | Strain: DOT-T1E-PhoA5 |
|---|---|---|
| Glucose | 85 | 91 |
| Citrate | 92 | 180 |
| Succinate | 125 | 125 |
| Glycerol | 459 | 464 |

*Doubling time in minutes in the exponential growth phase

Although the PhoA5 strain grew with a generation time similar to that of the wild-type strain in liquid LB medium (i.e. 45-50 min) it did not form colonies on solid LB medium. However, both the mutant and the wild-type formed colonies on solid M9 minimal medium with glucose, citrate or glycerol as the sole carbon source.

Effect of the Addition of Fe-Citrate:

Adding Fe-citrate restored the colony-forming ability of DOT-T1E-PhoA5 in LB agar medium, and growth of the PhoA5 mutant strain was impaired in the presence of the iron chelator ethylenediamine-di (o-hydroxyphenylacetic acid) (EDDHA). The ability of the mutant strain to produce colonies on solid LB was assayed by adding 30 or 300 μL per plate of a 0.06% solution of Fe-citrate. The strain formed well-defined colonies in 24 h, as did the wild-type. The effect of the presence of an iron chelator was tested on growth under conditions in which "iron-deficiency" was not so critical (e.g., M9 minimal-medium with glucose). Cells of the wild-type and PhoA5 mutant strains were pre-cultured on M9 minimal medium without iron supplementation, and with glucose (0.5% wt/vol) as the sole carbon source. Cultures were diluted 100-fold in the same medium in the absence and in the presence of 3 μg/mL EDDHA; in this latter case some cultures were also supplemented with iron (6 and 60 μg/mL Fe-citrate). The wild-type strain grew under all culture conditions, whereas growth of the PhoA5 mutant was severely inhibited in the presence of the iron chelator. This inhibition was overcome by adding Fe-citrate. These results confirm the deficiency of iron acquisition in the PhoA5 mutant strain.

Effect of Iron Addition on the Growth of pHBA by PhoA5 and its Role in pHBA Tolerance.

It was also tested whether growth on PHBA could be restored by adding a similar amount of Fe-citrate (60 μg/L), and whether this concentration had any effect on pHBA tolerance. In this series of assays, cultures of the wild-type and the mutant PhoA5 strains, growing on glucose as a carbon-source in the late log phase, were spread (0.1 mL) on M9 minimal medium plates with a gradient of 0 to 10 g/L pHBA, and the plates were or were not supplemented with iron. It was found that the wild-type strain formed a thick, colorless layer on the plates. In contrast, the mutant strain did not grow at all on the plates without iron supplementation, and only slight growth was observed on the plates with iron. It was also found that the plates on which the mutant was spread turned violet-purple. It was also tested whether iron had any effect on the survival of the PhoA5 mutant upon sudden pHBA shock. To this end the wild-type and PhoA5 mutant strains were grown on M9 minimal medium with glucose. When the culture reached a turbidity of about 1 at 660 nm, the cultures were split into two halves; one half served as a control and Fe-citrate was added to the other half. A series of aliquots were then prepared and pHBA was added to reach 0, 6, 12 and 18 g/L pHBA concentration. Survival following the pHBA shock was monitored by determining the changes with time in the number of CFU/mL.

The pattern of survival of the wild-type was similar both in the presence and in the absence of extra iron. In contrast, the presence of iron had a significant effect on the survival of the mutant. For example, a 12 g/L PHBA shock led to the survival of about 0.0001% of mutant cells in the absence of iron, whereas With extra iron survival approached 100%. At a higher concentration (i.e 18 g/L) no cells survived a shock in the absence of iron, whereas 0.001% of the cells did survive the shock when the culture had been supplemented with iron. These results suggest that although iron is not essential for pHBA tolerance in the wild-type strain, it helps the PhoA5 mutant to overcome the toxic effects of this aromatic carboxylic acid.

Tolerance of DOT-T1E to Aromatic Carboxylic Acid Derivatives

Tolerance/sensitivity to aromatic carboxylic acids was tested on double diffusion solid M9 minimal medium with 0.5% (wt/vol) glucose and the test compound in a gradient between 0 and 20 g/L. The wild-type and the PhoA-5 mutant were grown overnight on M9 minimal medium with glucose. One hundred μL were spread on plates (0-2 g/L gradient) and incubated for 20 h at 30° C., and growth was examined. The wild-type strain was found to be significantly more tolerant than the mutant strain to all benzene derivatives tested: o-, m-, and p-methoxybenzoate; p-methylbenzoate; o-, m- and p-aminobenzoate; o-, m-, and p-chlorobenzoate. The level of tolerance of the wild-type and the mutant strain are shown in Table 7.

TABLE 7

Pattern of sensitivity to aromatic carboxylic acid derivatives of *Pseudomonas putida* DOT-T1E and its mutant PhoA5

| | Strain | |
|---|---|---|
| Compound | Wild-type | PhoA5 |
| o-methoxybenzoate | 17 | 8.5 |
| m-methoxybenzoate | 12 | 7.2 |
| p-methoxybenzoate | 19 | 9.1 |
| p-methylbenzoate | 14.5 | 7.4 |
| o-aminobenzoate | 8.7 | 5.0 |
| m-aminobenzoate | 14.8 | 7.5 |
| p-aminobenzoate | 13.0 | 7.8 |
| o-chlorobenzoate | 14.5 | 6.0 |
| m-chlorobenzoate | 4.5 | 3.0 |
| p-chlorobenzoate | 11.7 | 4.0 |

The numbers indicate the concentration (g/L) that the strains tolerated.

Tolerance of DOT-T1E and DOT-T1E-PhoA5 to Organic Solvents with a $logP_{OW}$ Value Between 4.5 and 2.8

The growth of the wild-type *Pseudomonas putida* DOT-T1E and its mutant derivative DOT-T1E-PhoA5 was tested on liquid LB medium as follows: Cells were grown overnight on LB, then the culture was diluted 100-fold in the same culture medium (220 mL) and incubated for 2 h at 30° C. with agitation. Then the culture was split into 7×30 mL aliquots each. One aliquot was kept as a control and one of the following solvents was added to each of the others to reach a concentration of 0.3% (vol/vol): heptane (log Pow=4.5); propylbenzene (log Pow=3.6); cyclohexane (log Pow=3.2); ethylbenzene (log Pow=3.1); p-xylene (log Pow=3.0); and, 1-octanol (log Pow=2.8). Growth was monitored after 24 h incubation as turbidity of the cultures at 660 nm. Both the wild-type and the mutant tolerated all these solvents as the turbidity of all the cultures was above 1.5 units.

Tolerance of DOT-T1E and DOT-T1E-PhoA5 to Toluene

Previous studies (Ramos et al., *J. Bacteriol.* 180:3323-3329 (1998)) showed that preadaptation to toluene supplied via the vapor phase plays a key role in toluene tolerance (log Pow=2.5). DOT-T1E and DOT-T1E-PhoA5 were cultivated on minimal medium with glucose as the sole carbon-source with and without toluene in the gas phase. Cultures were challenged with 0.3% (vol/vol) toluene when they reached a turbidity of about OD660=1 and the cultures' short-term survival determined. For the wild-type strain sudden exposure of the non-pre-exposed cells to toluene led to a loss of viability (5 orders of magnitude), whereas pre-exposed cells tolerated the shock. The PhoA5 mutant was more sensitive and a lower survival rate of cells was observed both with non- and pre-exposed cells.

Tolerance to Aromatic Amino Acids of the Wild-Type and the PhoA5 Mutant Strain with or without pPAT7 (Construction Contained in Example 5).

The assay was done on M9 minimal medium plates with glucose as the carbon-source and a linear gradient of the three indicated amino acids in the range of 0 to 50 g/L. The results obtained are shown in Table 8. It can be observed that while the wild-type tolerated about 40 g/L, 35 g/L and 31 g/L of tyrosine, tryptophan and histidine respectively, the mutant strain only tolerated about 23 g/L of each of the above cited amino acids.

Tolerance to Aromatic Amino Acids by Different *Pseudomonas putida* Strains

All strains were grown on M9 minimal medium with glucose as the sole carbon source until they reached mid-exponential growth phase. Then, serial dilutions were spread on double diffusion solid M9 minimal medium plates with glucose (0.5% wt/vol) and a gradient (0 to 50 g/L) of the corresponding amino acid. The numbers indicate the tolerance (g/L) to the corresponding amino acid.

TABLE 8

| Strain | Tyrosine | Tryptophan | Histidine |
| --- | --- | --- | --- |
| T1E | 39.4 | 35.3 | 31.2 |
| T1E pPAT7 | 36.5 | 38.8 | 30.6 |
| PhoA5 | 25.3 | 23.5 | 22.3 |
| PhoA5 pPAT7 | 36.5 | 22.9 | 29.4 |

Tolerance to Alkylparabens of the Wild-Type and the PhoA5 Mutant Strain

The assay was done on M9 minimal plates with glucose as the carbon-source and a linear gradient of the methyl-ethyl-, propyl-, and butyloparabens. The parabens were supplied at the highest possible concentration, namely, 2 g/L, 1.54 g/L, 0.8 g/L and 0.3 g/L for methyl-, ethyl-, propyl- and butylparaben, respectively. The results obtained are shown in Table 9. It can be observed that the wild-type strain tolerated the highest tested concentrations of all parabens; however, the mutant tolerated only about 1 g/L methylparaben and 1.4 g/L ethylparaben, while it tolerated at least 0.8 g/L and 0.3 g/L propyl- and butylparaben, respectively.

TABLE 9

Tolerance to Parabens by Different *P. putida* Strains

| Strain | MB | EB | PB | BP |
| --- | --- | --- | --- | --- |
| T1E | >2 | >1.54 | >0.8 | >0.3 |
| T1E pPAT7 | >2 | >1.54 | >0.8 | >0.3 |
| PhoA5 | 1.0 | 1.4 | >0.8 | >0.3 |
| PhoA5 pPAT7 | >2.0 | 1.54 | >0.8 | >0.3 |

Abbreviations: MB, EB, PB and BP stand for methyl-, ethyl-, propyl- and butylparabene, respectively.

All strains were grown on M9 with glucose as the sole carbon source until they reached the mid-exponential growth phase. Serial dilutions were spread on double diffusion solid M9 plates with glucose (0.5% wt/vol) and a gradient of 0-2 g/L methylparaben and 0-1.54 g/L ethylparaben. The numbers indicate the tolerance g/L to the corresponding paraben.

The results presented above indicate that the mini-Tn5-'phoA transposon is inserted into a gene whose product is essential for utilizing pHBA as the carbon source, iron acquisition and tolerance to a number of drugs, including antibiotic and toxic chemicals. Therefore, altering the level of this gene product can have a beneficial effect in increasing tolerance to all the above series of cited chemicals.

Example 5

Genetic Characterization of the PhoA5 Mutant with an Altered Pattern of Sensitivity to p-Hydroxybenzoate The present Example describes methods for cloning of the mutation that leads to pHBA sensitivity and sequencing of the DNA adjacent to the mini-Tn5 insertion.

Total DNA of the PhoA5 mutant, which shows increased sensitivity to pHBA with respect to the wild-type strain, was digested with SphI. This cuts once between the 'phoA gene and the Km resistance marker so that DNA downstream from the Km marker can be recovered after ligation to pUC18 DNA as Km$^R$ colonies. A southern hybridization assay with the Km gene as a probe marked with digoxigenine revealed a 6.0 kb band. Based on these data, total DNA was digested with SphI and DNA in the range of 6.0 kb was ligated to SphI-digested pUC18. Then DNA was transformed into *E. coli* DH5 α, and Km$^R$ transformants were selected. One clone called pPAT5, was retained for further studies (FIG. 1).

Given that the sequence of the border of the mini-Tn5 is known, a primer was designed to sequence the adjacent DNA. About 900 bp were sequenced. The DNA was translated into a protein sequence and compared to proteins deposited in databanks. The DNA downstream revealed that the knocked-out gene encoded a protein homologous to the ExbD protein, which was followed by open reading frames (ORFs) homologous to the gene encoding the TonB protein.

To complete the DNA sequence of the cluster, a primer-walking strategy based on determining stretches of sequences followed by the design of primers made sequencing possible on both strands. In all, 2650 bp of the *Pseudomonas putida* DOT-T1E DNA were sequenced. Analysis of DNA for open reading frames (ORFs) revealed three stretches of 989, 428, and 731 bp, respectively. These ORFs extended from position 448 to 1438, 1442 to 1870, and 1867 to 2598 in the sequence. The close proximity of the end and the start of the first and the second ORFs and the overlapping nature of the second and the third ORF suggest that they are likely to form a single transcriptional unit. All three ORFs started with a canonical ATG for the first methionine of the polypeptides, and were preceded by potential Shine-Dalgano sequences (PuGGC). SEQ ID NO:3, 5, and 7 represent the deduced polypeptide sequence encoded by SEQ ID NO:2, 4, and 6 respectively. When these sequences were compared with those deposited at the GeneBank (See Tables 2, 3 and 4), the greatest homology of these polypeptides was to the ExbB, ExbD and TonB proteins of *Pseudomonas putida* WCS358 and to similar proteins of *Vibrio cholerae, Escherichia coli*, and other microorganisms.

Rescue of the Wild-Type exbBexbDtonB Gene Cluster

The following approach was used to rescue the whole gene cluster: first, the total DNA of DOT-T1E was digested with BamHI, HindIII, PstI and SalI, and (after transfer to nylon membranes) these fragments were hybridized against the tonB gene. The smallest hybridizing band (4.3 kb) was found with PstI. The corresponding region was recovered from an agarose gel and a library of 4.3 kb PstI fragments in plasmid pJB3-Tc was constructed. Two positive clones hybridizing to tonB were found. These clones were found to be identical after restriction digestion analysis. The resulting plasmid was called pPAT7 (FIG. 2).

Plasmid pPAT7 has been transferred to the wild-type strain and to the PhoA5 mutant strain as follows: *Pseudomonas putida* PhoA5 was mated with *E. coli* DH5α (pPAT7) and the helper strain *E. coli* (pRK600). Plasmid pRK600 is a suicide vector in *Pseudomonas* that serves to mobilize pPAT7 into the host strain. PhoA5 (pPAT7) transconjugants were selected on M9 minimal medium with glucose, 25 μg/L Km, and 12 μg/L Tc. Neither of the two *E. coli* strains grew in this medium. One of the transconjugants was retained.

The following set of assays with PhoA5 (pPAV) were performed:

1. The mutant strain with pPAT7 was tested for growth on minimal medium with pHBA and whether it has an effect on PHBA utilization by the wild-type. The mutant strain bearing pPAT7 recovered the ability to use pHBA as the sole carbon-source, as it produced colonies on minimal medium plates with 6 g/L of pHBA.
2. The PhoA5 mutant bearing pPAT7 was tested for an ability to produce colonies on LB. The results were positive.
3. The clone's ability to restore tolerance to pHBA and its effect on pHBA tolerance in the wild-type strain was also tested on double diffusion plates. The PhoA5 strain bearing pPAT7 recovered the ability to tolerate up to 15 g/L pHBA on plates, similar to the tolerance level of the wild-type strain with and without pPAT7 under the same assay conditions. It was also found that once the strain bears the exbBexbDtonB cluster in pPAT7, the presence of iron has no significant effects on the strain's pHBA tolerance.
4. The PhoA5 (pPAT7) mutant strain were tested for restored toluene tolerance to the PhoA5 mutant strain. The cells received a toluene shock after growth on LB or LB with toluene in the gas phase. pPAT7 partially restored tolerance to toluene shocks, since the number of viable cells of strain PhoA5 (pPAT7) was between the tolerance of the wild-type (the highest tolerance) and that of the mutant (the lowest tolerance). This identified the exbBDtonB gene cluster as an element controlling tolerance to aromatic compounds.
5. The PhoA5 (pPAT7) strain was tested for restored tolerance to metoxylated, amino and chlorinated aromatic carboxylic acids, and p-0methylbenzoate. The assays were done on double diffusion plates and revealed that PhoA5(pPAT7) was as tolerant as the wild-type to o-, m-, and p-methoxybenzoate, o-, m-, and p-chlorobenzoate, o-, m-, and p-aminobenzoate, and p-methylbenzoate.
6. Incorporating pPAT7 in the wild-type strain did not influence tolerance to aromatic amino acids; however, when pPAT7 was transferred to PhoA5, the strain-tolerated tyrosine and histidine at a level similar to that of the wild-type strain, although it remained more sensitive than the wild-type to tryptophan (Table 8).
7. The PhoA5 (pPAT7) strain was tested for restored tolerance to methyl- and ethylparaben. The assays were done on double diffusion plates and it was found that PhoA5 (pPAT7) was as tolerant as the wild-type strain to these two parabens (Table 9).

Example 6

Increasing Tolerance to pHBA of Different *Pseudomonas* Strains by Increasing the Copy Number of the exbBexbDtonB Cluster via pPAT7 and pPAT8 pPAT8, a derivative of the medium copy number pGV1120 plasmid carrying the exbBexbDtonB cluster, was constructed. FIG. 3 shows a scheme of this plasmid. Plasmids pPAT7 or pPAT8 were electroporated into the *P. putida* strains DOT-T1E PhoA5, KT2440 and into *P. mendocina* KR1 and the tolerance level to pHBA was tested on the double diffusion plates with a-gradient between 0 and 20 g/L pHBA. DOT-T1E with and without pPAT7 or pPAT8 tolerated about 17 g/L pHBA. *P. putida* KT2440 (pPAT8) was slightly more tolerant to pHBA than the wild-type strain or the strain with pPAT7. Introducing pPAT7 or pPAT8 into the PhoA5 mutant strain restored tolerance to PHBA to a level similar to that of the wild-type strain (Table 10). For *P. mendocina* the increase in the copy number of the exbBD-tonB cluster via plasmids pPAT7 or pPAT8 resulted in an increase in PHBA tolerance from about 8.5 g/L to 10 g/L.

TABLE 10 pHBA Tolerance of Different *Pseudomonas* Strains

| | Plasmid | | |
|---|---|---|---|
| Strain* | None | PpAT7 | pPAT8 |
| *P. putida* DOT-T1E | 17 | 17 | 17 |
| *P. putida* PhoA5 | 5 | 16 | 17 |
| *P. mendocina* KR1 | 8.5 | 10 | 10.2 |
| *P. putida* KT2440 | 17 | 17 | 18.5 |

*All strains were grown on M9 minimal medium until they reached exponential growth phase. Then serial dilutions were spread on double diffusion solid M9 minimal medium plates.

Example 7

The exbB, exbD and tonB in *Pseudomonas putida* DOT-T1E Form an Operon

Wild-type and PhoA5 cells were grown on M9 minimal medium with glucose (0.5% wt/vol) as the sole carbon source and mRNA-DNA free was prepared basically as described by Marqués et al., (*Biochim. Biophys. Acta* 1216:

227-236 (1993)). Then amplification assays using RT-PCR (Mosqueda, G., and J. L. Ramos, *J. Bacteriol.* 182: in press (2000)) and primers based on exbB and exbD or exbD and tonB (See FIG. 4) were done. The results revealed that exbB and exbD are part of the same transcript as are exbD and tonB. Therefore, it follows that exbB, exbD, and tonB are part of the same operon. As expected in the phoA5 mutant a transcript due to exbB and exbD genes could be amplified, but not that of exbD and tonB as expected from the location of mini-Tn5phoA at the 3'-end of the exbD genes. These results unequivocally show that the *P. putida* exb, exbD, and tonB genes transcribe a single mRNA.

Example 8

Selection of pHBA and Toluene Tolerant Mutants

| Selection of pHBA and Toluene Tolerant Mutants | | |
|---|---|---|
| General Methods: | | |
| Medium | | |
| $KH_2PO_4$ | 0.35 g/L | |
| $Na_2HPO_4$ | 1.5 g/L | |
| $NH_4Cl$ | 3.0 g/L | |
| Trace metals | 20 mL/L | Sterilize separately |
| Glucose | 5 g/L | Sterilize separately |
| Yeast extract | 0.48 g/L | Sterilize separately |
| $MgSO_4 \cdot 7H_2O$ | 0.492 g/L | Sterilize separately |
| HEPES | 25 mM | |
| DD $H_2O$ | 1 L | |
| pH 7.2, titration with KOH | | |

Trace metals (50-fold concentrated)

To about 150 mL water add 5 g citric acid, then add the following:

| | | |
|---|---|---|
| $CaCl_2 \times 2H_2O$ | 1.46 g | |
| $MnCl_2 \times 4H_2O$ | 0.4 g | |
| $Na_2MoO_4 \times 2H_2O$ | 0.1 g | |
| $FeSO_4 \times 7H_2O$ | 0.4 g | |
| $CuSO_4 \times 5H_2O$ | 0.1 g | |
| $ZnSO_4 \times 7H_2O$ | 0.2 g | |
| $CoCl_2 \times 6H_2O$ | 0.1 g | |

Adjust the volume to 200 mL.

Selection in Flasks:

Enrichment culture was used for selecting of acetate-tolerant strain. One hundred twenty five sealed flasks with 5 mL of medium (specified above) were used for these studies. Acetate (50-200 mM) and toluene (100 ppm) were added to the specified concentrations. The amount of toluene added was to reach the specified concentration in the liquid after equilibrium with air. After 11 transfers, during which the concentration of acetate was gradually increased, an adapted strain was obtained which was able to grow at 200 mM acetate, albeit at a slow rate. This culture was then used for further selection on plates.

Using a similar procedure with toluene, a toluene-tolerant strain (with a slow rate of growth on 150 ppm of toluene) was obtained. Adding 10 mM $MgSO_4$ increased the tolerance of the organism to toluene.

Selection and Characterization of Strains in Plates:

Five transfers were made on glass plates with trypticase soy agar (TSA-Difco) medium with 10 g/L glucose. Toluene (~0.5 mL) was added to the bottom of the inverted plates, saturating the medium and the gas phase. The plates were then transferred to a glass desicator and were incubated at 30° C. Four specific colonies were selected at this stage. pHBA was added to the plates in the last transfer and showed growth at 7 and 12 g/L pHBA, but not at 17 g/L pHBA. Three more transfers were made in the same medium with increasing concentrations of pHBA and replacing the toluene with an overlay of dodecane:toluene mixture (262 mL:26.5 mL). This mixture was calculated to give 100 ppm toluene concentration in the liquid phase. Enriched cultures grew at 20 g/L pHBA. Testing the culture from the last transfer showed growth in flasks at 100 ppm toluene and 20 g/L pHBA.

Three more transfers were made in a TSA medium plus 10 g/L glucose, 100 mg/L cycloheximide, 5 g/L agar (Difco), and increasing concentrations of pHBA. The pH was adjusted to 7.2. Toluene to 100 ppm was added to the bottom of the glass desicator as a mixture of hexadecane:toluene (262 mL:26.5 mL). This mixture was expected to give 100 ppm toluene in the liquid phase in equilibrium. Selected strains C and F (DGL#325) grew on 40 g/L pHBA after few day of incubation, strain C grew at 50 g/l pHBA after 10 days of incubation. Under microscope strain C grew in long chains. Test on TSA agar plates plus 25 µg/mL kanamycin and 10 µg/mL streptomycin, the antibiotic markers for *P. mendocina* KRC16 KDpobA 51 showed good growth for strain F and no growth for strain C.

Characterization of Tolerant Strains:

The strains *P. mendocina* KRC16 KDApob51 (#303), *P. mendocina* KRC16 KDApob51-F (#325), *P. putida* ATCC 29607 (#329) and *Pseudomonas putida* NRRL B-18435 (#332) were tested for growth at inhibitory concentrations of PHBA and toluene. The seed and the growth studies were done in 125 mL sealed flasks and 5 mL medium (see composition above), supplemented with 10 mM $MgSO_4$ and 5 g/L glucose. Flasks were incubated at 30° C. and 250 rpm. Toluene and pHBA were added in various concentrations. Growth was estimated based on harvesting the flasks at a specified time and measuring cell concentration after filtration, washing, oven drying, and weighing. For studies with non-adapted culture the seed culture was used after 24 h, while for the pre-adapted culture, the seed culture was used after 48 h with the addition to the medium of 60 ppm toluene and 5 g/L pHBA.

Table 11 compared the growth of non-adapted cultures at various concentrations of toluene and pHBA. Strain #325 the tolerant mutant, had better growth over the parent strain in all concentrations tested. Strain #332 has an advantage over Strain #303 at intermediate concentrations of toluene and pHBA and Strain #325 has an advantage over Strain #332 at high pHBA concentrations.

Table 12 compared the growth of pre-adapted cultures at various concentrations of toluene and pHBA. Here again Strain #325 has better growth over the parent strain in all concentrations tested. Strains #328 and #332 did not showed any significant difference over Strain #303 after pre-adaptation.

TABLE 11

The effect of toluene and pHBA on growth with non-adapted cultures

| Culture | 24 h[a] Toluene:pHBA[b] 0 ppm:0 g/L Growth (%) | 48 h[a] Toluene:pHBA[b] 60 ppm:10 g/L Growth (%) | 72 h[a] Toluene:pHBA[b] 60 ppm:20 g/L Growth (%) | 72 h[a] Toluene:pHBA[b] 0 ppm:20 g/L Growth (%) |
|---|---|---|---|---|
| #303 | 100 | 14 | 9 | 7 |
| #325 | 100 | 51 | 38 | 44 |
| #329 | 100 | 17 | 5 | 19 |
| #332 | 100 | 58 | 5 | 5 |

[a] = incubation time
[b] = added to medium

TABLE 12

The effect of toluene and pHBA on growth with preadapted cultures

| Culture | 24 h[a] Toluene:pHBA[b] 0 ppm:0 g/L Growth (%) | 48 h[a] Toluene:pHBA[b] 60 ppm:10 g/L Growth (%) | 72 h[a] Toluene:pHBA[b] 60 ppm:20 g/L Growth (%) | 72 h[a] Toluene:pHBA[b] 0 ppm:20 g/L Growth (%) |
|---|---|---|---|---|
| #303 | 100 | 44 | 8 | 12 |
| #325 | 100 | 55 | 24 | 26 |
| #328 | 100 | 18 | 6 | 14 |
| #329 | 100 | 58 | 13 | 14 |
| #332 | 100 | 26 | 12 | 13 |

[a] = incubation time
[b] = compounds and concentration added to medium

*Pseudomonas mendocina* (#303) and *Pseudomonas putida* DOT-T1E (#348) were compared under similar conditions. The medium used was described above. Strain #348T stands for stock of DOT-T1E that grew up with 100 ppm toluene and 5 g/L pHBA. Table 13 summarizes these results. Strain #348 grew better than Strain #303 at any concentration of toluene and pHBA. The difference at toluene:pHBA concentrations of 60:20 and 0:20 was actually higher because of extensive lysis at the time of harvesting the cells.

TABLE 13

**Tolerance to pHBA and toluene in *P. mendocina* #303, *putida* DOT-T1E (#348 and #348T)**

| | Toluene:PHBA (ppm & g/L) | Incubate Time (hr) | Growth (g/L) | Avg. Growth (g/L) | Growth (%) | Comments |
|---|---|---|---|---|---|---|
| #303 | | | | | | |
| 1 | 0:0 | 24 | 2.38 | 2.34 | 100 | Homogenous, very |
| 1 | 0:0 | 24 | 2.30 | | | few clumps |
| 2 | 60:10 | 48 | 0.92 | 1.00 | 43 | many small |
| 2 | 60:10 | 48 | 1.08 | | | clumps |
| 3 | 60:20 | 72 | 0.34 | 0.34 | 15 | little growth |
| 3 | 60:20 | 72 | 0.34 | | | |
| 4 | 0:20 | 72 | 0.30 | 0.30 | 13 | little growth |
| 4 | 0:20 | 72 | 0.30 | | | |
| #348 | | | | | | |
| 1 | 0:0 | 24 | 2.94 | 2.86 | 100 | Homogeneous, |
| 1 | 0:0 | 24 | 2.78 | | | no clumps |
| 2 | 60:10 | 48 | 2.30 | 2.11 | 72 | Some small clumps, |
| 2 | 60:10 | 48 | 1.92 | | | more turbid than 303 |
| 3 | 60:20 | 72 | 1.00 | 1.13 | 40 | Brownish color, |
| 3 | 60:20 | 72 | 1.26 | | | lysis |
| 4 | 0:20 | 72 | 0.88 | 0.90 | 31 | Lysis |
| 4 | 0:20 | 72 | 0.92 | | | |
| #348T | | | | | | |
| 1 | 0:0 | 24 | 2.96 | 2.94 | 100 | Homogeneous, |
| 1 | 0:0 | 24 | 2.92 | | | no clumps |
| 2 | 60:10 | 48 | 1.68 | 1.75 | 60 | some sm. Clumps, |

TABLE 13-continued

Tolerance to pHBA and toluene in *P. mendocina* #303,
*putida* DOT-T1E (#348 and #348T)

| | Toluene:PHBA (ppm & g/L) | Incubate Time (hr) | Growth (g/L) | Avg. Growth (g/L) | Growth (%) | Comments |
|---|---|---|---|---|---|---|
| 2 | 60:10 | 48 | 1.82 | | | more turbid than 303 |
| 3 | 60:20 | 72 | 1.50 | 1.58 | 54 | brownish color, lysis |
| 3 | 60:20 | 72 | 1.66 | | | |
| 4 | 0:20 | 72 | 1.72 | 1.32 | 45 | Lysis |
| 4 | 0:20 | 72 | 0.92 | | | |

Example 9

Screening and Characterization of Strains with High Tolerance to pHBA Protocol for Gradient Plates The strains were streaked on trypticase soy plus glucose plates and incubated at 30° C. overnight before the test.
Medium for Plates:

| | |
|---|---|
| $KH_2PO_4$ | 1.2 g |
| $(NH4)_2SO_4$ | 3 g |
| Bactoagar | 15 g |
| MOPS | 0.05 M from 1 M stock solution pH 7.2 |
| Adjust pH to 7.2. | |
| Autoclave at 121° C. for 20 minutes | |
| Add aseptically | |
| Glucose | 10 g from 50% solution |
| $MgSO_4 \times 7H_2O$ | 3 g (12.17 mL of 1 M stock solution) |
| Trace Elements | 10 mL (See below) |
| Yeast Extract | 10 mL (10% stock solution) |

The medium was steam sterilized and placed in a 50-60° C. water bath.

| Trace elements | g/L |
|---|---|
| Citric acid | 10 |
| $CaCl_2 \times 2H_2O$ | 1.5 |
| $FeSO_4 \times 7H_2O$ | 10 |
| $ZnSO_4 \times 7H_2O$ | 0.39 |
| $CuSO_4 \times 5H_2O$ | 0.38 |
| $Co\ Cl_2 \times 6H_2O$ | 0.2 |
| $Mn\ Cl_2 \times 4H_2O$ | 0.3 |
| Filter sterilized | |

To 100 mm×100 mm square petri plates, add 35 mL medium onto three plates. Allow to solidify overnight. Plates were placed on a 10 mL pipet to achieve the required slope. The same medium at x2 concentration was made, adjusted to pH 7.2, and left in 50-60° C. water bath. 200 g/L PHBA stock solution was prepared by suspending 200 g pHBA in 500 mL $H_2O$ and titrating with conc. KOH solution to pH ~7.2. The solution was filter sterilized and stored in dark. The pHBA solution was diluted to x2 to the required final concentration with DI water for plates and put in 50-60° C. water bath.

A 1:1 (vol:vol) mixture of the 2× medium and 2× pHBA solution was prepared and put in a water bath. Plates were then laid on a flat surface. Twenty-five mL of the mixture was pipetted to each plate and gel was left for a few hours.

Two loopfuls of the strains to be tested were suspended in 1 mL 0.9% saline and the gradient plates were streak from high concentration to low conc. Plates were incubated at 30° C. for 24 hr. Table 14 describes the growth of various strains on agar plates with a 0-40 g/L gradient of pHBA. The results (Table 14) showed a large spectrum of tolerance among the four strains tested. *P. putida* DOT-T1E is the most tolerant, followed by *E. coli* K12, and the two *P. mendocina* strains. No difference was observed between the wild-type parent strain *P. mendocina* KR1 and the pobA mutant *P. mendocina* krc16DKpobA51a.

TABLE 14

Growth of various strains on pHBA gradient plates

| | Temp. 30° C.; growth in mm | | | | | |
|---|---|---|---|---|---|---|
| Strain | Plate 1 | Plate 2 | Plate 3 | Plate 1 | Plate 2 | Plate 3 |
| *P. mendocina* krc16DkpobA51a (#303) | 10 | 10 | 10 | 10 | 10 | 15 |
| *Pseudomonas putida* DOT-T1E (#348) | 70 | 90 | 90 | 35 | 25 | 35 |
| *P. mendocina* KR1 (#363) | 10 | 10 | 20 | 10 | 10 | 10 |
| *E. coli* K12 (#327) | 35 | 35 | 35 | 20 | 35 | 35 |

The gradient was from 0 to 40 g/L and the plates were incubated for 24 h.

A similar test on agar plates with chloramphenicol (CAM) gradient plates showed a similar order of tolerance (Table 15).

TABLE 15

Growth of various strains on chloramphenicol (CAM) gradient plates

| | Growth (distance in mm) on CAM gradient | |
|---|---|---|
| Strain | 0-50 mg/L | 0-100 mg/L |
| *P. mendocina* krc16DkpobA51a (#303) | 15 | 15 |
| *P. putida* DOT-T1E (#348) | 90 | 90 |
| *P. mendocina* KR1-A (#362) | 15 | 15 |
| *P. mendocina* KR1-A (#362) | 10 | 15 |
| *P. mendocina* krc16DkpobA51a (#303) | 40 | 10 |
| *P. putida* DOT-T1E (#348) | 90 | 90 |
| *P. mendocina* KR1-A (#362) | 15 | 10 |
| *P. mendocina* KR1-A (#362) | 25 | 10 |

TABLE 15-continued

Growth of various strains on chloramphenicol (CAM) gradient plates

| Strain | Growth (distance in mm) on CAM gradient | |
|---|---|---|
| | 0-50 mg/L | 0-100 mg/L |
| P. mendocina krc16DkpobA51a (#303) | 30 | 10 |
| P. putida DOT-T1E (#348) | 90 | 90 |
| P. mendocina KR1-A (#362) | 45 | 15 |
| P. mendocina KR1-A (#362) | 45 | 15 |

Screen for pHBA Tolerance or Sensitivity

The test was done on rectangular Petri dishes with a gradient of PHBA between 0 and 30 g/L. The sensitive strains were: *Ralstonia solanacearum, Pseudomonas stutzeri, Pseudomonas fluorescens, Bacillus subtilis, Pseudomonas aeruginosa, Pseudomonas vesicularis, Alcaligenes eutrophus*. The tolerant strains were: *Acinetobacter calcoaceticus, Pseudomonas putida* EEZ10, *Escherichia coli* ET8000, *Pseudomonas putida* R1. The pHBA tolerance in these strains was similar to *P. putida* DOT-T1E and *P. putida* KT2440.

---

What is claimed is:

1. An isolated nucleic acid encoding only an ExbD polypeptide from *Pseudomonas*, having a nucleotide sequence selected from the group consisting of:
   (a) the nucleotide sequence of SEQ ID NO:4;
   (b) a nucleotide sequence encoding the amino acid sequence of SEQ ID NO:5; and
   (c) a nucleotide sequence that is 95% identical to the nucleotide sequence of SEQ ID NO:4;
   or a nucleic acid having a nucleotide sequence that is 100% complementary to the full length nucleotide sequence of (a), (b), or (c) above.

2. The isolated nucleic acid of claim 1, comprising the nucleotide sequence of SEQ ID NO:4.

3. The isolated nucleic acid of claim 1 operably linked to at least one regulatory sequence.

4. An isolated bacterial cell transformed with the isolated nucleic acid of claim 3.

5. The transformed bacterial cell of claim 4, wherein the bacterial cell is *E. coli, Pseudomonas* sp., *Pseudomonas mendocina*, or *Pseudomonas putida*.

* * * * *